United States Patent
Böttcher et al.

(10) Patent No.: US 11,596,626 B2
(45) Date of Patent: Mar. 7, 2023

(54) **COMPOUND FOR USE AGAINST PATHOGENIC *NEISSERIA* AND *HAEMOPHILUS* SPECIES AND *MORAXELLA CATARRHALIS***

(71) Applicant: Universität Konstanz, Constance (DE)

(72) Inventors: Thomas Böttcher, Constance (DE); David Szamosvari, Constance (DE); Christof Hauck, Constance (DE); Tamara Schuhmacher, Constance (DE); Petra Muenzner-Voight, Constance (DE)

(73) Assignee: Universität Konstanz, Constance (DE)

( * ) Notice: Subject to any disclaimer, the term of this patent is extended or adjusted under 35 U.S.C. 154(b) by 121 days.

(21) Appl. No.: 16/768,828

(22) PCT Filed: Dec. 14, 2018

(86) PCT No.: PCT/EP2018/084954
§ 371 (c)(1),
(2) Date: Jun. 1, 2020

(87) PCT Pub. No.: WO2019/121392
PCT Pub. Date: Jun. 27, 2019

(65) Prior Publication Data
US 2021/0169869 A1    Jun. 10, 2021

(30) Foreign Application Priority Data
Dec. 22, 2017  (EP) .................................. 17002066

(51) Int. Cl.
A61K 31/47    (2006.01)
A61P 31/04    (2006.01)
A01N 43/42    (2006.01)

(52) U.S. Cl.
CPC .............. *A61K 31/47* (2013.01); *A01N 43/42* (2013.01); *A61P 31/04* (2018.01)

(58) Field of Classification Search
CPC .......... A61K 31/47; A61P 31/04; A01N 43/42
See application file for complete search history.

(56) References Cited

U.S. PATENT DOCUMENTS

| 3,547,949 A | 12/1970 | Malen | |
| 7,442,798 B2 * | 10/2008 | Pesci ........................ | C12N 1/20 |
| | | | 546/153 |
| 10,961,196 B2 * | 3/2021 | Böttcher ................ | G01N 21/64 |

FOREIGN PATENT DOCUMENTS

| WO | 99/52890 A1 | 10/1999 |
| WO | 02/18342 A2 | 3/2002 |
| WO | 2004/092154 A1 | 10/2004 |
| WO | 2008/060865 A2 | 5/2008 |
| WO | 2015/116492 A1 | 8/2015 |

OTHER PUBLICATIONS

Patel, J Clin Pharmacol, vol. 56(9), 1060-1075, 2016. (Year: 2016).*
Tristram, CLin Microb Rev, Apr. 2007, 368-389. (Year: 2007).*
Abraham, W-R., "Going Beyond the Control of Quorum-Sensing to Combat Biofilm Infections", Antibiotics, 2016, vol. 5(3), pp. 1-16.
Braveny, V.I., et al., "In-vitro-Aktivitat von Rosoxacin (Win 35 213) Gegen Neisseria Gonorrhoeae", Arzneim.-Forsch./Drug Res., 1980, vol. 30(9), pp. 1476-1478 (English abstract included).
Gales, A., et al, "Activities of BMS 284756 (T-3811) Against Haemophilus influenzae, Moraxella catarrhalis, and *Streptococcus pneumoniae* Isolates from SENTRY Antimicrobial Surveillance Program Medical Centers in Latin America (1999)", Antimicrobial Agents and Chemotherapy, May 2001, vol. 5(5), pp. 1463-1466.
Hayashi, K., et al., "Synthesis, Antibacterial Activity, and Toxicity of 7-(Isoindolin-5-yl)-4-oxoquinoline-3-carboxylic Acids", Arzneim.-Forsch./Drug Res., 2002, vol. 52(12), pp. 903-913.
Kapić, S., et al., "6-Alkylquinolone-3-carboxylic Acid Tethered to Macrolides Synthesis and Antimicrobial Profile", Bioorganic and Medicinal Chemistry, 2010, vol. 18(17), pp. 6569-6577.
Kapić, S., et al., "Synthesis of Macrolones with Central Piperazine Ring in the Linker and it's Influence on Antibacterial Activity", Bioorganic and Medicinal Chemistry, 2011, vol. 19(23), pp. 7281-7298.
Takahata, M., et al., "In Vitro and In Vivo Antimicrobial Activities of T-3811ME, a Novel Des-F(6)-Quinolone", Antimicrobial Agents and Chemotherapy, May 1999, vol. 43(5), pp. 1077-1084.
Wang, T., et al., "Design, Synthesis and Biological Evaluation of Potent NAD-dependent DNA Ligase Inhibitors as Potential Antibacterial Agents. Part II: 4-amino-pyrido[2,3-d]pyrimidin-5(8H)-ones", Bioorganic and Medicinal Chemistry Letters, 2012, vol. 22(11), pp. 3699-3703.
Wube, A.A., et al., "Synthesis of N-substituted 2-[(1-E)-alkenyl]-4-(1H)-quinolone Derivatives as Antimycobacterial Agents Against Non-Tubercular Mycobacteria", European Journal of Medicinal Chemistry, 2011, vol. 46(6), pp. 2091-2101.

(Continued)

*Primary Examiner* — D Margaret M Seaman
(74) *Attorney, Agent, or Firm* — McDonnell Boehnen Hulbert & Berghoff LLP

(57) ABSTRACT

The present invention relates to a compound, which can be used in the prevention and treatment of infections with pathogenic *Neisseria* species, in particular *N. gonorrhoeae* and *N. meningitidis* (the gonococcus and the meningococcus, respectively), and other pathogenic bacteria (e.g. *Haemophilus* species or *Moraxella catarrhalis*), and which can be used for disinfecting a substrate from said bacteria. Moreover, the present invention relates to a corresponding pharmaceutical composition comprising said compound.

(1)

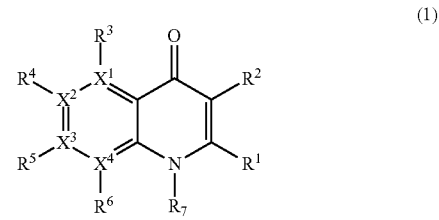

17 Claims, 14 Drawing Sheets

(56) References Cited

OTHER PUBLICATIONS

Wube, A.A., et al., "Design, Synthesis and Antimycobacterial Activities of 1-methyl-2-alkenyl-4(1H)-quinolones", Bioorganic and Medicinal Chemistry, 2011, vol. 19(1), pp. 567-579.
Zahra, J.A., et al., "Heterocycles [H]-Fused to 4-Oxoquinoline-3-Carboxylic Acid. Part IX, Synthesis of 2,6-Dioxotetrahydro-1H-Pyrrolo[3,2-H]Quinoline-7-Carboxylic Acid", Heterocycles, 2011, vol. 83(9), pp. 2165-2175.
Extended European Search Report for European Patent Application No. 17002066.3, dated Mar. 6, 2018, pp. 1-14.
Written Opinion for Application No. PCT/EP2018/084954, filed Dec. 14, 2018, pp. 1-7.
Unemo M., et al., "Treatment Failure of Pharyngeal Gonorrhea with Internationally Recommended First-Line Ceftriaxone Verified in Slovenia Sep. 2011", Euro Surveill., 2012, vol. 17(25). [Retrieved from the internet on Jun. 2, 2020: <URL:https://www.eurosurveillance.org/content/10.2807/1560-7917.ES.2019.24.24.1900354>].
Edwards, M., et al., "Antigenic Analysis of Gonococcal Pili Using Monoclonal Antibodies", J. Exp. Med., 1984, vol. 160(6), pp. 1782-1791.
Muenzner, P., et al., "Human-Restricted Bacterial Pathogens Block Shedding of Epithelial Cells by Stimulating Integrin Activation", Science, Sep. 3, 2010, vol. 329(5996), pp. 1197-1201.
Rajan, N., et al., "Characterization of an Immortalized Human Vaginal Epithelial Cell Line", The Journal of Urology, Feb. 2000, vol. 163, pp. 616-622.
Borges, M., et al., "Photobiological Properties of Hydroxy-Substituted Flavothiones", Photochemistry and Photobiology, 2002, vol. 75(2), pp. 97-106.
Calfee, M.W., et al., "Interference with Pseudomonas Quinolone Signal Synthesis Inhibits Virulence Factor Expression by Pseudomonas Aeruginosa", Proc. Natl. Acad. Sci. USA, 2001, vol. 98(20), pp. 11633-11637.
Cathcart, G.R., et al., "Inhibitor Profiling of the Pseudomonas Aeruginosa Virulence Factor LasB Using N-alpha Mercaptoamide Template-Based Inhibitors", Bioorganic & Medicinal Chemistry Letters, 2009, vol. 19(21), pp. 6230-6232, doi:10.1016/j.bmcl.2009.08.099, Epub Sep. 10, 2009. (Abstract only).
Detty, M.R., "Preparation of "Unnatural" Tellurium Analogues of Naturally Occurring Chromones and Flavones. The Control of Ipso vs. Ortho Acylation, Selective Demethylation, and Olefin-Forming Condensation Reactions in Benzo[b] tellurapyranones", Organometallics, 1988, vol. 7(10), pp. 2188-2197.
Majumdar, K.C., et al., "Synthesis of Thiochromen-4-one-annelated Heterocycles:Regioselective Cyclization of 3-Hydroxy-2-cyclohex-2'-enylthiochromen-4-one", Synthetic Communications, 2006, vol. 33(1), pp. 133-142, doi:10.1081/SCC-120015569.
Mughal, Ehsan Ullah, et al., "Synthesis and Antibacterial Activity of Substituted Flavones, 4-Thioflavones and 4-Iminoflavones", Bioorganic & Medicinal Chemistry, 2006, vol. 14(14), pp. 4704-4711.
Nakazumi, Hiroyuki, et al., "Synthesis and Antibacterial Activity of 2-Phenyl-4H-benzo[b]thiopyran-4-ones (Thioflavones) and Related Compounds", J. Heterocyclic Chem., 1984, vol. 21(1), pp. 193-196.
Sashida, Haruki, "An Alternative Facile Preparation of Telluro-and Selenochromones from o-Bromophenyl Ethynyl Ketones", Synthesis, May 1998, pp. 745-748.
International Preliminary Report on Patentability, received from the International Bureau of WIPO, dated Jan. 3, 2019, for International Application No. PCT/EP2017/000735, pp. 1-11.
Szamosvári, D., et al., "A Thiochromenone Antibiotic Derived from the Pseudomonas Quinolone Signal Selectively Targets the Gram-Negative Pathogen Moraxella catarrhalis", Chem. Sci., 2019, vol. 10, pp. 6624-6628.
Shen et al.," Palladium-Catalyzed Carbonylative Four-Component Synthesis of Thiochromenones: The Advantages of a Reagent Capsule," Agnew. Chem. Int. Ed., 2016, vol. 55, pp. 5067-5070.
Matsumoto et al., "Thiochromones as, etc.," Chem. Abstracts, 1975, 83:109785.
Hirao et al., "Reactions of a-Lithiatd 4H-1-Benzothiopyran-4-one and 1,2-Dihydrocyclopenta [b] [1] Benzothiopyran-9(3H)-One Derrivatives," Bull. Chem. Soc. Jpn., 1985, vol. 58, pp. 2203-2206.
Huang et al., "A New Synthetic Route to Florine-Containing Thiochromones," Heteroatom Chemistry, 1995 vol. 6, No. 3, pp. 287-291.
Nussmaumer et al., "2-Substituted 4-(Thio) Chromenone 6-0-Sulfamates: Potent Inhibitors of Human Steroid Sulfatase," J. Med. Chem., 2002, vol. 45, No. 19, pp. 4310-4320.
Willy et al., "Microwave-assisted Three-Component Coupling-Addition-SnAr (CASNAR) Sequences to Annelated 4H-Thiopyran-4-ones," Org. Biomol. Chem., 2010, vol. 8, pp. 90-95.
Yang et al., "Domino reactions of 1-(2-alkoxyaryl)-3-akylprop-2-yn-1-ones with Sodium Sulfide Leading to thiochromen-4-one Derivatives," RSC Advances, 2012, vol. 2, pp. 6549-6554.
Narayan et al., "Hypervalent Iodine-Meditated Selective Oxidative Functionalization of (Thio)chromones with Akanes," Chem. Eur. J., 2014, vol. 20, pp. 4567-4572 and supporting information.
Inami et al., "Nickel-catalyzed Reaction of Thioisatins and Alkynes: A Facile Synthesis of Thiochromones," Org. Lett., 2014, vol. 16, pp. 5660-5662 and supporting information, pp. S1-S78.
Majumdar et al., "Thiochromenone-Annelated Heterocycles: Regioselective Synthesis of Furo[3, 2-b]-thiochromen-9-ones," Monatshefte fur Chemie, 2001, vol. 132, pp. 739-746.

* cited by examiner

| | NQ | | | | NQNO | | | | trans-Δ¹-NQ | | | | trans-Δ¹-NQNO | | | |
|---|---|---|---|---|---|---|---|---|---|---|---|---|---|---|---|---|
| [μM] | 5 | 10 | 25 | 50 | 5 | 10 | 25 | 50 | 5 | 10 | 25 | 50 | 5 | 10 | 25 | 50 |
| Neisseria gonorrhoeae 0959000081 DGI | | | | | | | | | | | | | | | | |
| Neisseria gonorrhoeae 0359000014 DGI | | | | | | | | | | | | | | | | |
| Neisseria gonorrhoeae kl. Isolate Ngo_LSH1 | | | | | | | | | | | | | 0.8 | | | |
| Neisseria lactamica | | | | | | | | | | | | | 0.7 | | | |
| Neisseria gonorrhoeae 0659000011 DGI | | | | | | | | | | | | | 0.7 | | | |
| Neisseria gonorrhoeae VPI | | | | | | | | | | | | | 0.9 | | | |
| Moraxella catarrhalis | | | | | | | | | 0.9 | | | | | | | |
| Neisseria gonorrhoeae 1259000231 AB Res | | | | | | | | | | | | | 0.8 | | | |
| Neisseria gonorrhoeae MS11 | | | | | | | | | | | | | 1.0 | 0.7 | | |
| Neisseria gonorrhoeae 0159000241 DGI | | | | | | | | | | | | | 1.0 | 0.8 | | |
| Neisseria meningitidis | 0.5 | | | | 0.5 | 0.5 | | | | | | | 1.0 | 0.5 | | |
| Neisseria gonorrhoeae cl. isol Ngo_LSH3 | 0.6 | 0.5 | | | 0.7 | 0.6 | | | | | | | 0.9 | | | |
| Haemophilus parainfluenzae | | | | | | | | | | | | | 0.6 | 0.5 | | |
| Neisseria gonorrhoeae 1259000340 DGI | | | | | | | 0.5 | 0.6 | | | | | 0.5 | | | |
| Neisseria gonorrhoeae cl. isol Ngo_LSH2 | 0.6 | 0.5 | 0.5 | | 0.7 | 0.6 | 0.6 | | | | | | 1.0 | 0.6 | | |
| Haemophilus haemolyticus | | | | | 0.5 | | | | 0.8 | 0.8 | 0.6 | | 0.8 | 0.8 | 0.6 | |
| Neisseria gonorrhoeae 1159000316 AB res | | | 0.5 | | | 0.6 | 0.5 | 0.6 | 0.7 | 0.5 | | | 1.0 | 0.9 | | |
| Neisseria flavescens | | | | | | 0.5 | | | 0.9 | 0.9 | 0.8 | 0.7 | 1.0 | 0.9 | 0.5 | |
| Neisseria gonorrhoeae 0559000102 DGI | 0.7 | 0.5 | 0.5 | 0.5 | 0.8 | 0.8 | 0.6 | 0.7 | | | | | 1.1 | 1.0 | 0.7 | |
| Neisseria weaveri | | | | 0.5 | 0.5 | 0.5 | 0.7 | 0.7 | | | | 0.6 | 2.1 | 1.5 | | |
| Haemophilus influenzae | 0.9 | 0.7 | 0.5 | 0.7 | 0.6 | 1.0 | 0.7 | 0.7 | 0.5 | 0.5 | 0.5 | 0.5 | 0.7 | 0.6 | 0.4 | |
| Neisseria mucosa | 0.7 | 0.7 | 0.7 | 0.8 | 0.7 | 0.7 | 0.8 | 0.7 | 0.6 | 0.6 | 0.6 | 0.6 | 0.6 | 0.6 | 0.6 | 0.5 |
| Neisseria subflava | | | | | 0.9 | 0.5 | | | 1.1 | 1.0 | 0.8 | 0.9 | 1.0 | 1.1 | 0.9 | |
| Neisseria perflava | 0.5 | | | | 0.6 | 0.6 | 0.7 | 0.7 | 1.0 | 1.0 | 0.9 | 0.9 | 1.0 | 1.0 | 0.7 | |
| Neisseria sicca | 0.5 | 0.5 | 0.5 | 0.6 | 0.6 | 0.6 | 0.7 | 0.7 | 0.9 | 0.8 | 0.9 | 0.9 | 0.9 | 0.8 | 0.6 | |
| Neisseria elongata elongata | 0.9 | 0.7 | 0.8 | | 0.9 | 0.9 | 0.7 | 0.7 | 0.8 | 0.8 | 0.8 | 0.9 | 0.7 | 0.5 | 0.7 | |
| Neisseria macacae | 0.9 | 0.9 | 0.9 | 0.9 | 0.8 | 0.8 | 0.9 | 0.9 | 0.8 | 0.7 | 0.8 | 0.8 | 0.8 | 0.6 | 0.5 | 0.5 |
| Neisseria dentiae | 0.8 | 0.8 | 0.7 | 0.7 | 0.8 | 0.8 | 0.8 | 0.8 | 1.0 | 0.9 | 0.9 | 1.0 | 0.9 | 0.9 | 0.9 | 0.7 |
| Neisseria canis | 0.8 | 0.8 | 0.8 | 0.9 | 0.9 | 0.9 | 0.8 | 0.7 | 0.9 | 0.9 | 0.9 | 0.9 | 1.0 | 1.0 | 0.9 | 0.8 |
| Neisseria cinerea | 1.0 | 1.0 | 1.0 | 0.8 | 1.0 | 1.0 | 0.9 | 0.9 | 1.1 | 1.0 | 1.0 | 0.9 | 1.0 | 1.0 | 0.9 | 0.8 |

Figure 5

COMPOUND FOR USE AGAINST PATHOGENIC *NEISSERIA* AND *HAEMOPHILUS* SPECIES AND *MORAXELLA CATARRHALIS*

CROSS-REFERENCE

This application is a 371 U.S. national phase of PCT/EP2018/084954, filed Dec. 14, 2018, which claims priority from EP patent application no. 17002066.3, filed Dec. 22, 2017, both which are incorporated by reference in its entirety.

FIELD OF THE INVENTION

The present invention relates to a compound, which can be used in the prevention and treatment of infections with pathogenic *Neisseria* species, in particular *N. gonorrhoeae* and *N. meningitidis* (the gonococcus and the meningococcus, respectively), and other pathogenic bacteria (e.g. *Haemophilus* species or *Moraxella catarrhalis*), and which can be used for disinfecting a substrate from said bacteria. Moreover, the present invention relates to a corresponding pharmaceutical composition comprising said compound.

BACKGROUND OF THE INVENTION

The enormous power of antibiotics in combating infectious diseases has sustained unprecedented advances in medicine and contributed to the increases in life expectancy and overall quality of life of the human population. However, there are alarming signs that the protection afforded by antibiotics is on the decline. This is particularly true for a growing number of bacterial pathogens, which have become resistant to the majority of antimicrobial drugs. Some strains even have acquired resistances against all available antibiotics rendering infections by these "super-bugs" virtually untreatable. While antibiotic resistance is on the rise, the number of newly approved antibiotics has continuously declined and the industrial pipeline is by and large empty. Two facts contribute to this shortage: First, the majority of existing antibiotics target only very few cellular targets. Second, the existing antibiotics belong to a small number of distinct chemical classes. Consequently, resistance development is fast, cross-resistances are common, and evolved resistance genes can be mobilized by horizontal gene transfer (HGT) to additional bacterial species. Discovering both new antibiotic classes and new cellular targets is thus a prime goal for the future treatment of bacterial infections.

Based on the global disease burden and the associated societal and economic costs, the world health organization WHO has released a priority list of bacterial pathogens, where there is an urgent need of novel treatment options. These species require particular attention due to the lack of available vaccines and the increasing occurrence of multi-drug resistant strains and thus should be in the focus of current national and international efforts to device and further develop novel ways of protection and/or treatment.

One pathogen, which the WHO has identified as high priority, is *Neisseria gonorrhoeae*, the causative agent of the genital tract infection gonorrhoea. With an estimated 80 million affected people annually, gonorrhoea is one of the most common sexually transmitted diseases. Caused by the human-restricted pathogen *Neisseria gonorrhoeae*, infections cannot only trigger an acute inflammatory response in the genital tract, but can also lead to disseminated disease and infertility in both sexes. Furthermore, gonococcal infections promote the spread of HIV.

*N. meningitidis* is a closely related pathogen, which is the causative agent of bacterial meningitis. Meningococcal meningitis is a severe, life-threatening disease, which belongs to the reportable infectious diseases. In Germany, the annual incidence ranges below 0.5 cases/100.000 people, while annual meningococcal epidemics are known from the sub-Saharan "meningitis belt" in Africa with approximately 30.000 cases annually. Fortunately, *N. meningitidis* infections can be prevented by vaccination.

In contrast, a vaccine against *N. gonorrhoeae* is not available and the gonococcus has already developed resistances against most antibiotics including ciprofloxacin. The only remaining treatment options for gonococcal infections are based on ceftriaxone, an extended-spectrum cephalosporin requiring intravenous application. However, also first resistances against this current last-resort antibiotic have been reported and the complete lack of additional treatment options poses an imminent threat. Thus, novel antibiotics against *N. gonorrhoeae* are urgently required. Preferably, such compounds should be also effective against multi-resistant *N. gonorrhoeae* and against the closely related pathogen *Neisseria meningitidis*, but should not affect non-pathogenic, commensal Neisseriae. Such a species-selective antibiotic compound could for example reduce the risk of fast resistance development in commensal non-target species and the transfer via HGT to the pathogenic Neisseriae species, the gonococcus and the meningococcus. Since *N. gonorrhoeae* is associated with a defined clinical picture and can be readily diagnosed, a species-specific antibiotic could be of enormous value in this indication and reduce the risk of resistance development in commensal non-target species.

Thus, the technical problem underlying the present invention is to provide a compound, which can be used in the prevention and treatment of infections with pathogenic *Neisseria* species and/or other pathogenic bacteria such as *Haemophilus* species or *Moraxella catarrhalis*, preferably in the treatment of infections with pathogenic and/or multi-resistant species, as well as a corresponding pharmaceutical composition.

SUMMARY OF THE INVENTION

The solution to the above technical problem is achieved by the embodiments characterized in the claims.

The present invention relates to a compound which can be used in the prevention and treatment of infections with pathogenic *Neisseria* species, for example *N. gonorrhoeae* and *N. meningitidis*, and/or other pathogenic bacteria (e.g. *Haemophilus* species or *Moraxella catarrhalis*), and which can be used for disinfecting a substrate from said bacteria. The present invention also relates to a pharmaceutical composition and methods of use in the prevention and treatment of infections. The compound is represented by the general Formula (1) or a pharmaceutically acceptable salt thereof:

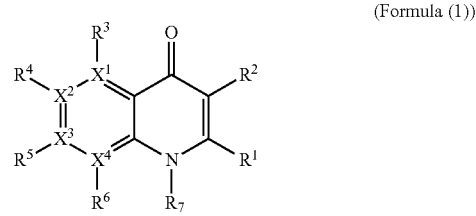

(Formula (1))

DESCRIPTION OF THE DRAWINGS

FIG. 5: Determination of the inhibitory effect of the compounds represented by the Formulas (4) to (7) against various bacterial species. Effective inhibition of growth ≥60% (values 0.0 to 0.4) is indicated by black shading. Values represent integrals of growth curves relative to a control (1.0).

DETAILED DESCRIPTION OF THE INVENTION

Figure 1:
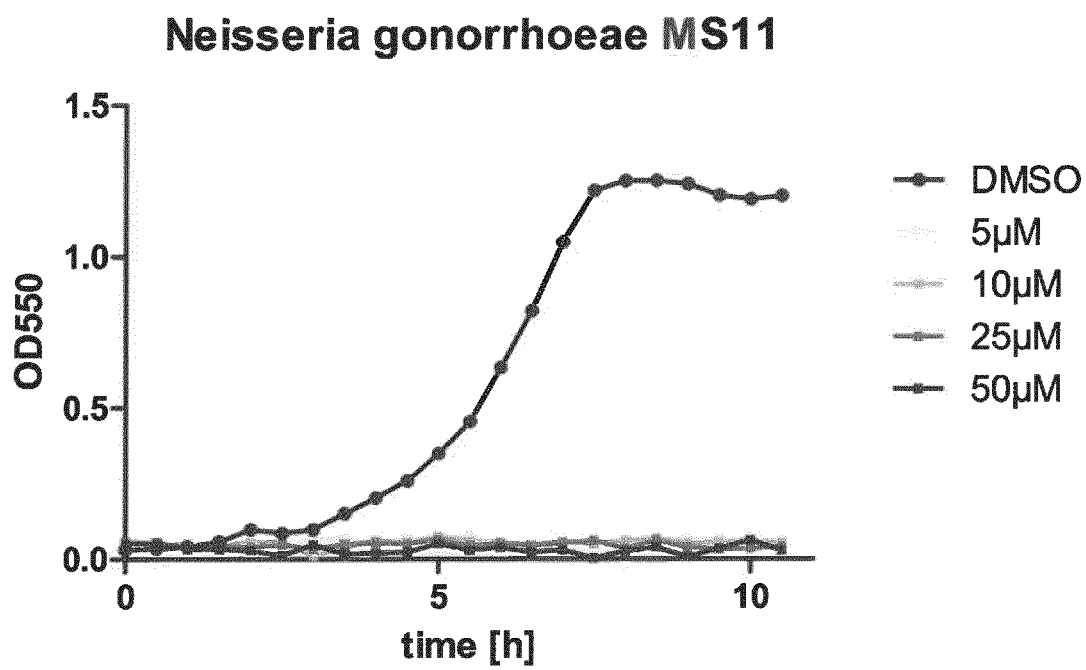
FIG. 1: Growth curves of *Neisseria gonorrhoeae* MS11 in the presence of different concentrations of NQNO (control: treatment with DMSO).

In particular, the present invention relates to a compound for use in the prevention and treatment of infections with pathogenic *Neisseria* species, for example *N. gonorrhoeae* and *N. meningitidis*, and/or other pathogenic bacteria (e.g. *Haemophilus* species or *Moraxella catarrhalis*), wherein the compound is represented by the general Formula (1) or a pharmaceutically acceptable salt thereof

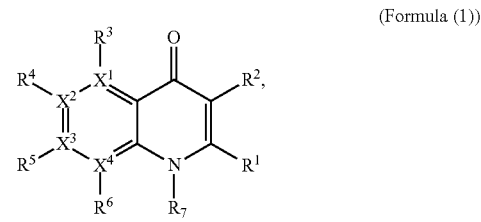

(Formula (1))

wherein
$R^1$ is selected from the group consisting of a substituted or unsubstituted alkyl group having from 3 to 20 carbon atoms, a substituted or unsubstituted cycloalkyl group having from 4 to 12 carbon atoms, a substituted or unsubstituted alkenyl group having from 3 to 20 carbon atoms, a substituted or unsubstituted cycloalkenyl group having from 4 to 12 carbon atoms, a substituted or unsubstituted alkynyl group having from 3 to 20 carbon atoms, a substituted or unsubstituted aryl group, and a substituted or unsubstituted heteroaryl group;

$R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, and —OA, wherein A is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$R^2$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, —$NZ^1Z^2$, —$NO_2$, —ON, —$OZ^3$, —$C(O)Z^4$, —$C(O)NZ^5Z^6$, —$COOZ^7$, and —$SO_3Z^8$, wherein $Z^1$ to $Z^6$ and $Z^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group and $Z^7$ is selected from the group consisting of a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group;

$X^1$ to $X^4$ are each independently selected from a carbon atom and a nitrogen atom with the proviso that the respective $R^3$ to $R^6$ is absent, when the corresponding $X^1$ to $X^4$ is a nitrogen atom; and $R^3$ to $R^6$, when present, are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, —$NE^1E^2$, —$NO_2$, —ON, —$OE^3$, —$C(O)E^4$, —$C(O)NE^5E^6$, $COOE^7$, and —$SO_3E^8$, wherein $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group.

The compound for use according to the present invention may also be present in the corresponding tautomeric form (e.g. in the form of 4-hydroxyquinolines), if applicable.

If not stated otherwise, such as for example partially for the residue $R^1$, the following definitions apply to the terms "halogen", "alkyl group", "cycloalkyl group", "alkenyl group", "cycloalkenyl group", "alkynyl group", "aryl group", and "heteroaryl group". Herein the term "halogen" refers particularly to fluorine atoms, chlorine atoms, bromine atoms, and iodine atoms, preferably fluorine atoms and chlorine atoms, most preferably fluorine atoms. The term "alkyl group" refers particularly to a branched or linear alkyl group having 1 to 20, preferably 1 to 12, more preferably 1 to 6, and most preferably 1 to 4 carbon atoms, which can be substituted or unsubstituted. Examples of alkyl groups represent methyl groups, ethyl groups, propyl groups, isopropyl groups, butyl groups, isobutyl groups, tert-butyl groups, pentyl groups, hexyl groups, and heptyl groups. The term "cycloalkyl group" refers particularly to a cycloalkyl group having 3 to 10, preferably 4 to 8, more preferably 5 or 6, and most preferably 6 carbon atoms, which can be substituted or unsubstituted. Examples of cycloalkyl groups represent cyclobutyl groups, cyclopentyl groups, and cyclohexyl groups. The term "alkenyl group" refers particularly to a branched or linear alkenyl group having 2 to 20, preferably 2 to 12, more preferably 2 to 6, and most preferably 2 to 4 carbon atoms, which can be substituted or unsubstituted. Examples of alkenyl groups represent vinyl groups, allyl groups, 1-heptenyl groups, 2,6-dimethylhept-5-enyl groups, and crotyl groups. The term "cycloalkenyl group" refers particularly to a cycloalkenyl group having 4 to 10, preferably 5 to 8, more preferably 5 or 6, and most preferably 6 carbon atoms, which can be substituted or unsubstituted. Examples of cycloalkenyl groups represent cyclopentenyl groups, cyclopentadienyl groups, cyclohexyl groups, and cyclohexadienyl groups. The term "alkynyl group" refers particularly to a branched or linear alkynyl group having 2 to 20, preferably 2 to 12, more preferably 2 to 6, and most preferably 2 to 4 carbon atoms, which can be substituted or unsubstituted. Examples of alkynyl groups represent ethynyl groups, 1-propynyl groups, and propargyl groups. The term "aryl group" refers particularly to an aryl group consisting of 1 to 6, preferably 1 to 4, more preferably 1 to 3 aromatic rings, and most preferably 1 ring, which can be substituted or unsubstituted. Examples of aryl groups represent phenyl groups, anthracenyl or naphthyl groups. The term "heteroaryl group" refers particularly to a heteroaryl group consisting of 1 to 6, preferably 1 to 4, more preferably 1 to 3 aromatic rings including heteroatoms, which can be substituted or unsubstituted. Heteroatoms, which are present in heteroaryl groups are for example N, O and S. Examples of heteroaryl groups represent pyridyl groups, pyrimidinyl groups, thienyl groups, furyl groups or pyrrolyl groups.

According to the present invention, the alkyl groups, the cycloalkyl groups, the alkenyl groups, the cycloalkenyl groups, the alkynyl groups, the aryl groups and the heteroaryl groups may be substituted or unsubstituted. The potential substituents are not specifically limited. Accordingly, instead of hydrogen atoms any substituent known in the prior art can be bonded to the further positions of the corresponding groups. For example, the potential substituents may be selected from the group consisting of a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms, a halogen atom, —$NL^1L^2$, —$NO_2$, —ON, —$OL^3$, —$C(O)L^4$, —C(O)

NL$^5$L$^6$, —COOL$^7$, and —SO$_3$L$^8$, wherein L$^1$ to L$^8$ are each independently selected from a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms. Accordingly, examples of substituted alkyl groups are aralkyl groups or alkyl groups substituted with e.g. halogen atoms, such as e.g. a trifluoromethyl group or a trichloromethyl group, or any other of the above-mentioned substituents. The term "aralkyl group" refers particularly to an alkyl group wherein one or more hydrogen atoms, preferably terminal hydrogen atoms of the alkyl chain, are replaced by aryl or heteroaryl groups. Examples of aralkyl groups represent benzyl groups or 1- or 2-phenylethyl groups. Preferably, the potential substituents are selected from the group consisting of a branched or linear alkyl group having 1 to 6 carbon atoms, a branched or linear alkenyl group having 2 to 6 carbon atoms, a branched or linear alkynyl group having 2 to 6 carbon atoms, a halogen atom, —NH$_2$, —NHCH$_3$, —N(CH$_3$)$_2$, —NO$_2$, —OH, —OCH$_3$, —OEt, —C(O)H, —C(O)CH$_3$, —C(O)Et, and —COOH. Moreover, one or more tetravalent carbon atoms (together with the hydrogen atoms bonded thereto), when present, in each of the alkyl groups, the cycloalkyl groups, the alkenyl groups, the cycloalkenyl groups, and the alkynyl groups may each independently be substituted by a member selected from the group consisting of O, (OCH$_2$CH$_2$)$_n$O, S, (SCH$_2$CH$_2$)$_m$S, C(O), C(O)O, NR$^8$, and C(O)NR$^9$, preferably O, (OCH$_2$CH$_2$)$_n$O, C(O)O, and C(O)NR$^9$, wherein n and m are each independently an integer from 1 to 6. Accordingly, for example an alkyl group may be interrupted by e.g. one or more PEG linkers and/or amide bonds. The way the groups are introduced instead of a carbon atom is not specifically limited. For example, a carbon atom may be substituted by C(O)O in the sense of —C(O)O— or —OC(O)— and by C(O)NR$^9$ in the sense of —C(O)NR$^9$— or —NR$^9$C(O)—. According to the present invention, R$^8$ and R$^9$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms, —OG$^1$, —C(O)G$^2$, —C(O)NG$^3$G$^4$, —COOG$^5$, and —SO$_2$G$^6$. In a preferred embodiment, R$^8$ and R$^9$ are each independently selected from the group consisting of a hydrogen atom, a branched or linear alkyl group having 1 to 6 carbon atoms, an aryl group having 1 to 3 aromatic rings, —C(O)G$^2$, and —SO$_2$G$^6$. Most preferably, R$^8$ and R$^9$ are each independently selected from the group consisting of a hydrogen atom and a branched or linear alkyl group having 1 to 6 carbon atoms. According to the present invention, G$^1$ to G$^6$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 aromatic rings, a heteroaryl group having 1 to 3 aromatic rings including heteroatoms. In a preferred embodiment, G$^1$ to G$^6$ are each independently selected from the group consisting of a hydrogen atom, a branched or linear alkyl group having 1 to 6 carbon atoms, an aryl group having 1 to 3 aromatic rings.

Most preferably, the alkyl groups, the cycloalkyl groups, the alkenyl groups, the cycloalkenyl groups, the alkynyl groups, the aryl groups and the heteroaryl groups are unsubstituted. Moreover, in a preferred embodiment the alkyl groups, the alkenyl groups, and the alkynyl groups are linear.

The alkenyl groups, the cycloalkenyl groups and the alkynyl groups may possess multiple unsaturated bonds, which may be conjugated or unconjugated. Preferably, the alkenyl groups, the cycloalkenyl groups and the alkynyl groups each possess at least one unsaturated bond, preferably in $\Delta^1$ position (i.e. including the proximal carbon atom of the group to which the rest of the compound is attached). Compounds having an unsaturated bond in $\Delta^1$ position are advantageously highly active against the target bacteria. More preferably, the alkenyl groups, the cycloalkenyl groups and the alkynyl groups each possess only one unsaturated bond, preferably in $\Delta^1$ position.

The unsaturated bonds in the alkenyl groups and the cycloalkenyl groups may independently have cis- and/or trans-configuration. Preferably, the unsaturated bonds in the alkenyl groups have trans-configuration. Most preferably, the alkenyl groups possess one unsaturated bond with trans-configuration, preferably in $\Delta^1$ position.

The compound according to the present invention may be the compound represented by the general Formula (1) as described above or a pharmaceutically acceptable salt thereof. In case the compound of the present invention is a pharmaceutically acceptable salt of the compound according to general Formula (1), the salt can be formed with inorganic or organic acids or bases. Examples of pharmaceutically acceptable salts comprise, without limitation, non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfonate derived from p-toluenesulfonic acid, sodium salts, potassium salts, magnesium salts, calcium salts, iron salts, zinc salts, aluminum salts, ammonium salts, and others. Such salts can be readily produced by methods known to a person skilled in the art.

Other salts like oxalate derived from oxalic acid, which is not considered as pharmaceutically acceptable, can be appropriately used as intermediates for the production of the compound of the general Formula (1) or a pharmaceutically acceptable salt thereof or physiologically functional derivative or a stereoisomer thereof.

According to the present invention, $R^1$ is selected from the group consisting of a substituted or unsubstituted, branched or linear alkyl group having from 3 to 20, preferably 4 to 11, more preferably 6 to 10, most preferably 9 carbon atoms, a substituted or unsubstituted cycloalkyl group having from 4 to 12, preferably 6 to 9, most preferably 7 or 8 carbon atoms, a substituted or unsubstituted, branched or linear alkenyl group having from 3 to 20, preferably 4 to 11, more preferably 6 to 10, most preferably 9 carbon atoms, a substituted or unsubstituted cycloalkenyl group having from 4 to 12, preferably 6 to 9, most preferably 7 or 8 carbon atoms, a substituted or unsubstituted, branched or linear alkynyl group having from 3 to 20, preferably 4 to 11, more preferably 6 to 10, most preferably 9 carbon atoms, a substituted or unsubstituted aryl group, and a substituted or unsubstituted heteroaryl group. In a preferred embodiment, $R^1$ is selected from the group consisting of substituted or unsubstituted, branched or linear alkyl group having from 3 to 20, preferably 4 to 11, more preferably 6 to 10, most preferably 9 carbon atoms, a substituted or unsubstituted, branched or linear alkenyl group having from 3 to 20, preferably 4 to 11, more preferably 6 to 10, most preferably 9 carbon atoms, and a substituted or unsubstituted, branched or linear alkynyl group having from 3 to 20, preferably 4 to 11, more preferably 6 to 10, most preferably 9 carbon atoms. More preferably, $R^1$ is a substituted or unsubstituted, branched or linear alkyl group having 6 to 10, even more preferably 9 carbon atoms or a substituted or unsubstituted, branched or linear alkenyl group having 6 to 10, even more preferably 9 carbon atoms. More preferably $R^1$ is a heptyl, octyl, nonyl, heptenyl, octenyl, or nonenyl group. Most preferably R is a nonyl or nonenyl group. Preferably, the nonenyl group is a trans-$\Delta^1$-nonenyl group.

According to the present invention, $R^7$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, and —OA. Moreover, A is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably A is selected from the group consisting of a hydrogen atom, a substituted or unsubstituted alkyl group, and a substituted or unsubstituted aryl group. Most preferably, A is hydrogen. Preferably, R' is selected from the group consisting of a hydrogen atom, a substituted or unsubstituted alkyl group, a substituted or unsubstituted aryl group, and —OA. More preferably, $R^7$ is a hydrogen atom or OH.

According to the present invention, $R^2$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, $NZ^1Z^2$, —$NO_2$, —ON, —$OZ^3$, —$C(O)Z^4$, —$C(O)NZ^5Z^6$, —$COOZ^7$, and —$SO_3Z^8$. $Z^1$ to $Z^6$ and $Z^6$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably $Z^1$ to $Z^6$ and $Z^6$ are each independently selected from the group consisting of a hydrogen atom, a substituted or unsubstituted alkyl group, and a substituted or unsubstituted aryl group, most preferably $Z^1$ to $Z^6$ and $Z^8$ are each independently selected from the group consisting of a hydrogen atom and a substituted or unsubstituted alkyl group. $Z^7$ is selected from the group consisting of a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably $Z^7$ is selected from the group consisting of a substituted or unsubstituted alkyl group and a substituted or unsubstituted aryl group, most preferably $Z^7$ is a substituted or unsubstituted alkyl group. Preferably, $R^2$ is selected from the group consisting of a hydrogen atom, a substituted or unsubstituted alkyl group having 1 to 4 carbon atoms, a substituted or unsubstituted alkenyl group having 2 to 4 carbon atoms, a substituted or unsubstituted alkynyl group having 2 to 4 carbon atoms, a halogen atom, —$CF_3$, —$NH_2$, and —OH. Most preferably, $R^2$ is a hydrogen atom.

According to the present invention, $X^1$ to $X^4$ are each independently selected from a carbon atom and a nitrogen atom with the proviso that the respective $R^3$ to $R^6$ is absent, when the corresponding $X^1$ to $X^4$ is a nitrogen atom (for example, $R^3$ is absent, when $X^1$ is a nitrogen atom). Preferably, at most 2, more preferably at most 1, of X' to $X^4$ are/is a nitrogen atom. Most preferably, none of $X^1$ to $X^4$ is a nitrogen atom, i.e. each of $X^1$ to $X^4$ is a carbon atom.

According to the present invention, $R^3$ to $R^6$, when present, are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, —$NE^1E^2$, —$NO_2$, —ON, —$OE^3$, —$C(O)E^4$, —$C(O)NE^5E^6$, —$COOE^7$, and —$SO_3E^8$. $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably $E^1$ to $E^8$ are each independently selected from the group consisting of a hydrogen atom, a substituted or unsubstituted alkyl group, and a substituted or unsubstituted aryl group, most preferably $E^1$ to $E^8$ are each independently selected from the group consisting of a hydrogen atom and a substituted or unsubstituted alkyl group. Preferably, $R^3$ to $R^6$ are each independently selected from the group consisting of a hydrogen atom, a substituted or unsubstituted alkyl group, a substituted or unsubstituted alkenyl group, a substituted or unsubstituted alkynyl group, a halogen atom, —$NE^1E^2$, —$NO_2$, —$OE^3$, —$C(O)E^4$, and —$COOE^7$. More preferably, $R^3$ to $R^6$ are each independently selected from the group consisting of a hydrogen atom, a substituted or unsubstituted alkyl group, a substituted or unsubstituted alkenyl group, a substituted or unsubstituted alkynyl group, and a halogen atom. Most preferably, each of $R^3$ to $R^6$ is hydrogen.

In one preferred embodiment of the present invention, $R^7$ is H. In this embodiment, it is particularly preferred that $R^1$ is a substituted or unsubstituted, branched or linear alkyl group having from 3 to 20 carbon atoms, more preferably 4 to 11 carbon atoms, most preferably 9 carbon atoms, or a substituted or unsubstituted, branched or linear alkenyl group having from 3 to 20 carbon atoms, more preferably 4 to 11 carbon atoms, most preferably 9 carbon atoms. Preferably, $R^2$ is selected from the group consisting of a hydrogen atom, a substituted or unsubstituted alkyl group having 1 to 4 carbon atoms, a substituted or unsubstituted alkenyl group having 2 to 4 carbon atoms, a substituted or unsubstituted alkynyl group having 2 to 4 carbon atoms, a halogen atom, —$CF_3$, —$NH_2$, and —OH, and more preferably $R^2$ is a hydrogen atom. Furthermore, at most 1 of $X^1$ to $X^4$ is preferably a nitrogen atom, most preferably each of $X^1$ to $X^4$ is a carbon atom. Moreover, it is preferred in this embodiment that $R^3$ to $R^6$, when present, are each independently selected from the group consisting of a hydrogen atom, a halogen atom, and a trifluoromethyl group, more preferably each of $R^3$ to $R^6$, when present, is a hydrogen atom. In this embodiment, as examples, the present invention more preferably relates to a compound selected from the group consisting of the compound represented by the Formula (2) (i.e. HHQ), the compound represented by the Formula (4) (i.e. NQ), and the compound represented by the Formula (6) (i.e. trans-$\Delta^1$-NC)), more preferably to the compounds represented by the Formulas (4) and (6), and most preferably to the compound represented by the Formula (4), or a pharmaceutically acceptable salt thereof.

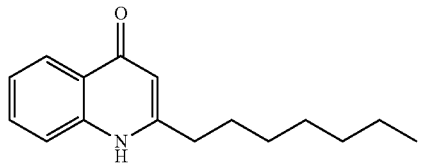

Formula (2)

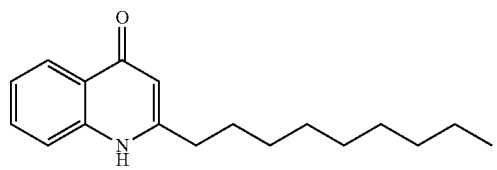

Formula (4)

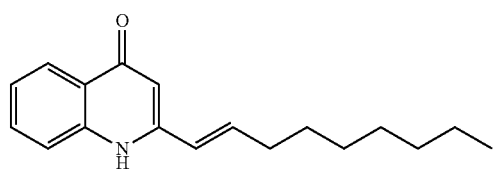

Formula (6)

In another preferred embodiment of the present invention, $R^7$ is —OA, and most preferably $R^7$ is —OH. In this embodiment, it is particularly preferred that $R^1$ is a substituted or unsubstituted, branched or linear alkyl group having from 3 to 20 carbon atoms, more preferably 4 to 11 carbon atoms, most preferably 9 carbon atoms, or a substituted or unsubstituted, branched or linear alkenyl group having from 3 to 20 carbon atoms, more preferably 4 to 11 carbon atoms, most preferably 9 carbon atoms. Preferably, $R^2$ is selected from the group consisting of a hydrogen atom, a substituted or unsubstituted alkyl group having 1 to 4 carbon atoms, a substituted or unsubstituted alkenyl group having 2 to 4 carbon atoms, a substituted or unsubstituted alkynyl group having 2 to 4 carbon atoms, a halogen atom, —$CF_3$, —$NH_2$, and —OH, and more preferably $R^2$ is a hydrogen atom. Furthermore, at most 1 of $X^1$ to $X^4$ is preferably a nitrogen atom; most preferably each of $X^1$ to $X^4$ is a carbon atom. Moreover, it is preferred in this embodiment that $R^3$ to $R^6$, when present, are each independently selected from the group consisting of a hydrogen atom, a halogen atom, and a trifluoromethyl group, more preferably each of $R^3$ to $R^6$, when present; is a hydrogen atom. In this embodiment, as examples, the present invention more preferably relates to a compound selected from the group consisting of the compound represented by the Formula (3) (i.e. HQNO), the compound represented by the Formula (5) (i.e. NQNO), and the compound represented by the Formula (7) (i.e. trans-$\Delta^1$-NQNO), more preferably to the compounds represented by the Formulas (5) and (7), and most preferably to the compound represented by the Formula (5), or a pharmaceutically acceptable salt thereof.

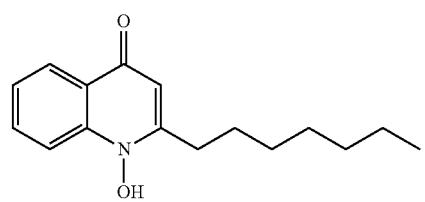

Formula (3)

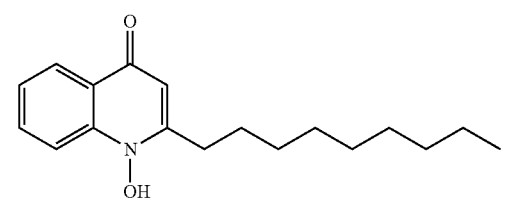

Formula (5)

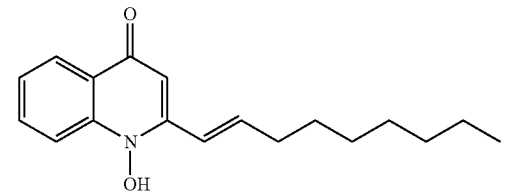

Formula (7)

The above embodiments can be combined with each other without any particular limitation. The above statements and definitions given with respect to the specific embodiments analogously apply to each respective embodiment when combined with the other embodiments. In this embodiment, as examples, the present invention more preferably relates to a compound selected from the group consisting of the compounds represented by the Formulas (2) to (7), more preferably to the compounds represented by the Formulas (4) and (5), or pharmaceutically acceptable salts thereof.

The pathogenic bacteria, which can be treated with the compound for use according to the present invention, are not particularly limited. For example, the pathogenic microbes may be selected from the genera *Neisseria, Haemophilus*, or *Moraxella*. Specifically, examples of (human) pathogens that can be treated with the compound for use according to the present invention are *Neisseria* gonorrhoea, *Neisseria meningitidis, Neisseria lactamica, Haemophilus influenzae,* and *Moraxella catarrhalis.* Furthermore, the compound for use according to the present invention can also be effective against other bacteria and fungi. Preferably, the compound for use according to the present invention only affects pathogenic species and e.g. not commensal non-target species, such as commensal members of the normal human mucosal flora. This can reduce the risk of resistance development in commensal non-target species. Examples of commensal non-target species are represented by, but are not limited to commensal Neisseriae. *Candida albicans, Lactobacillus crispatus, Gardnerella vaginalis,* and *Lactobacillus brevis,* preferably *Candida albicans* and *Lactobacillus brevis.* Preferably, the treatable pathogenic bacteria are selected from the group consisting of *Neisseria gonorrhoeae, Neisseria meningitidis, Neisseria lactamica,* and *Moraxella catarrhalis,* more preferably from *Neisseria gonorrhoeae* and *Neisseria meningitidis.* Most preferably, the treatable pathogenic bacteria are *Neisseria gonorrhoeae.*

In a further preferred embodiment, the treatable bacteria are multi-resistant bacteria, more preferably multi-resistant *Neisseria gonorrhoeae* and *Neisseria meningitidis,* more preferably multi-resistant *Neisseria gonorrhoeae.* Examples of multi-resistant *Neisseria gonorrhoeae* strains are represented by, but are not limited to, *Neisseria gonorrhoeae* multidrug-resistant isolate from Slovenia (Unemo M, Golparian D, Potočnik M, Jeverica S. Treatment failure of pharyngeal gonorrhoea with internationally recommended first-line ceftriaxone verified in Slovenia, September 2011. Euro Surveill. 2012; 17(25):pii=20200) or *Neisseria gonorrhoeae* multidrug-resistant isolate from Austria (Unemo M, Golparian D, Stary A, Eigentler A. 2011. First *Neisseria gonorrhoeae* strain with resistance to cefixime causing gonorrhoea treatment failure in Austria, 2011. Euro Surveill. 16(43). pii: 19998).

In a preferred embodiment, the compound for use according to the present invention has a minimum inhibitory concentration (MIC) against pathogenic bacteria species, preferably pathogenic *Neisseria* species, more preferably *Neisseria gonorrhoeae,* even more preferably multi-resistant *Neisseria gonorrhoeae* strains, of 50 µg/mL or less, more preferably 40 µg/mL or less, more preferably 30 µg/mL or less, more preferably 20 µg/mL or less, more preferably 15 µg/mL or less, most preferably 10 µg/mL or less. The lower limit of the minimum inhibitory concentration (MIC) is generally not specifically limited. For example, the lower limit of the minimum inhibitory concentration (MIC) may be 0.01 ng/mL.

In a further preferred embodiment, the compound for use according to the present invention leads to a growth reduction of pathogenic bacteria species, preferably pathogenic *Neisseria* species, more preferably *Neisseria gonorrhoeae,* even more preferably multi-resistant *Neisseria gonorrhoeae* strains, of at least 50%, more preferably at least 60%, more preferably at least 70%, more preferably at least 80%, more preferably at least 85%, more preferably at least 90%, more preferably at least 95%, more preferably at least 98%, most preferably 100% (i.e. complete inhibition), when compared to the corresponding untreated case. Said growth reduction can e.g. be achieved when the compound for use according to the present invention is applied in a dosage (e.g. in vivo) or concentration (e.g. in vitro) as indicated below.

The dosage of the compound for use according to the present application can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 µg/kg/day to 100 mg/kg/day animal body weight preferably 5 µg/kg/day to 50 mg/kg/day. Suitable dosage rates for larger mammals, for example humans, are of the order of from about 1 mg to 4 g/day, conveniently administered once, in divided doses such as e.g. 2 to 4 times a day, or in sustained release form. Moreover, the compound for use according to the present application can be applied topically to a locally defined site of infection, including but not limited to the urogenital tract, vaginal mucosa, or the nasopharynx. In these cases, different dosages may be applied directly to the site of infection ranging from 1 ng/application to 5 g/application, preferably 1 ng/application to 1 g/application, more preferably 1 ng/application to 100 mg/application. Applications may vary from a single dose application or one application per day or one application every second day, to several applications per day such as two, three, four or five applications/day.

The compound for use according to the present invention can be used in the prevention and treatment of an infection with pathogenic bacteria species, preferably pathogenic *Neisseria* species, more preferably *Neisseria gonorrhoeae,* even more preferably multi-resistant *Neisseria gonorrhoeae* strains, in mammals, and particularly preferably in humans.

In another aspect, the present invention relates to a pharmaceutical composition comprising the compound for use according to the present invention in a pharmaceutically active amount, and optionally a pharmaceutically acceptable carrier, excipient or diluent. The above statements and definitions analogously apply to this aspect of the present invention. The compound of the present invention can be administered per se or in the form of pharmaceutical preparations.

The term "medicament" as used herein relates to any pharmaceutical composition comprising at least the compound according to the present invention in a pharmaceutically active amount.

According to the present invention, the medicament may be administered by any administration route known in the art being suitable for delivering a medicament to a mammal. The route of administration does not exhibit particular limitations and includes for example oral application, topic application, intravenous application and intraperitoneal application. The compound also may be administered topically as ointment, by powders, drops or transdermal patch, or as an oral or nasal spray.

The concentration of the compound of the present invention in the pharmaceutical composition of the present invention is not particularly limited. Preferably, the concentration of the compound of the present invention in the pharmaceutical composition is from 0.1 µM to 5 M, more preferably from 5 µM to 5 M, and most preferably from 10 µM to 100 mM.

In another aspect, the present invention relates to the use of the compound used in the present invention for disinfecting a substrate from pathogenic *Neisseria* species, for example *N. gonorrhoeae* and *N. meningitidis,* and/or other pathogenic bacteria (e.g. *Haemophilus* species or *Moraxella catarrhalis*), wherein the substrate is selected from the group consisting of medical tools, medical equipment, floor, linen, paper, and medical and industrial surfaces. The above statements and definitions analogously apply to this aspect of the present invention. Preferably, the disinfection is not carried out at a human or animal body, i.e. is carried out in vitro.

The applied amount of the compound for disinfection is not particularly limited. For example, the compound may be applied in solution in a concentration of from 0.1 μM to 5 M, more preferably from 10 μM to 1 M, and most preferably from 10 μM to 100 mM. Solvents used for preparing corresponding solutions are not particularly limited and may e.g. be selected from the group consisting of DMSO, acetonitrile, N-methyl-2-pyrrolidone, cyclohexane, n-hexane, ethyl acetate, 1,2-dichloroethene, dichloromethane, xylene, and alcohols, such as methanol, ethanol, isopropanol, phenethyl alcohol and benzyl alcohol. Also liposome preparations may be used for formulation of the compound for disinfection.

The compound used in the present invention can selectively kill pathogenic *Neisseria* species, for example *N. gonorrhoeae* and *N. meningitidis*, and/or other pathogenic bacteria (e.g. *Haemophilus* species or *Moraxella catarrhalis*), preferably pathogenic *Neisseria gonorrhoeae* species, and has unprecedented efficacy. For example, growth of *N. gonorrhoeae* can, preferably completely, be inhibited in vitro and colonization of humanized mice can preferably be prevented, thereby preferably not affecting closely related *Neisseria* or beneficial bacteria. Moreover, at low micromolar concentrations pathogenic Neisseriae can e.g. selectively be killed, without harming commensal members of the normal human mucosal flora. Furthermore, no cytotoxicity in e.g. HeLa cells is preferably observed. In vivo application of the compound used in the present invention to the genital tract is e.g. well tolerated and prohibits colonization with *Neisseria gonorrhoeae* in a humanized mouse model. Moreover, topical administration of the compound at bactericidal concentrations to the mucosal surface of the genital tract of female mice does preferably not result in tissue damage, demonstrating that the compound is well tolerated and does not harm eukaryotic cells or tissue. Most commensal *Neisseria* are preferably not affected by the compound used in the present invention and the beneficial human microbiota are preferably not harmed by treatment with the compound. Nevertheless, with said compound it is even possible to treat infections based on multi-resistant *Neisseria* species, such as multi-resistant *N. gonorrhoeae* and *N. meningitidis*. Therefore, the compound used in the present invention shows unique activity, which suggests a novel mode of action. Thereby, it is for example possible to inhibit the promotion of HIV spread associated with *N. gonorrhoeae*.

The present invention will be further illustrated in the following examples without being limited thereto.

Experimental Procedures:
General

Chemicals and solvents for the synthesis were purchased from Sigma-Aldrich, Acros Organics, Carl Roth or VWR Chemicals and were used without further purification. For Silica gel chromatography, distilled technical grade solvents and silica gel 60 A (Carl Roth) was used. Thin layer chromatography (TLC) was performed using aluminum sheets "TLC Silica gel 60 F254" from Merck Millipore® and analyzed with UV-light or by permanganate staining. NMR spectra were obtained with Bruker Avance-III 400 and Bruker Avance-III 600 NMR spectrometers at ambient temperature. Multiplicities are given as follows: s—singlet, d—doublet, t—triplet, q—quartet, quint.—quintet, m multiplet. Chemical shifts (δ) are given in parts per million (ppm) relative to the solvent residual signal with CDCl$_3$ $δ_H$=7.26 ppm and $δ_C$=77.16 ppm, DMSO-d$_6$ $δ_H$=2.50 ppm and $δ_C$=39.52 ppm, MeOD-d$_4$ $δ_H$=3.31 ppm and $δ_C$=49.00 ppm. The obtained data were processed and analyzed with Bruker Topspin 3.5 software. Mass spectrometry data were obtained by ESI-TOF (Bruker Daltonics amicroTOFII) equipped with a Chromolith FastGaradient RP18e 50×2 mm (Merck) column or ESI-IT (Bruker Daltonics Esquire 3000plus) equipped with a Nucleoshell 50×2 mm RP-18 2.7 μm (Macherey-Nagel).

SYNTHESIS EXAMPLES

Synthesis of HHQ and NQ (Compounds represented by the Formulas (2) and (4)) as well as HQNO and NQNO (Compounds represented by the Formulas (3) and (5))

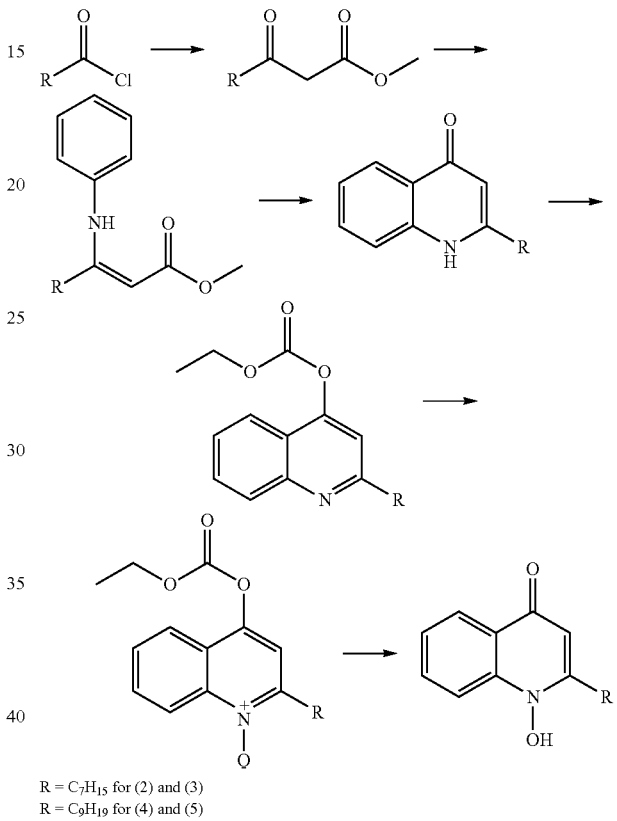

R = C$_7$H$_{15}$ for (2) and (3)
R = C$_9$H$_{19}$ for (4) and (5)

General Synthesis of β-Keto-Methyl Esters:

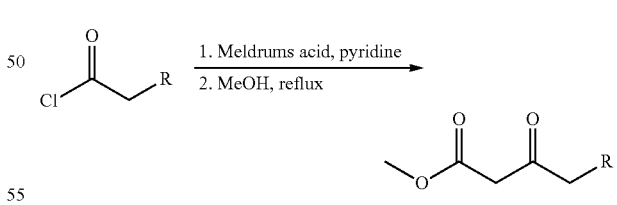

2,2-Dimethyl-1,3-dioxane-4,6-dione (Meldrum's acid) (37.0 mmol, 1 eq.) was dissolved in 50 ml DCM and cooled to 0° C. Pyridine (74.0 mmol, 2 eq.) was added and the reaction stirred for 20 min at 0° C. Acid chloride (37 mmol, 1 eq.) was added dropwise and the resulting orange/red solution was allowed to stir at 0° C. for 1 h and at room temperature for 1 h. After the reaction time, the mixture was washed with 5% HCl (3×60 ml) and the organic phases washed with brine (2×60 ml), dried over anhydrous MgSO$_4$, filtered and the solvent evaporated. The remaining brown oil was dissolved in 100 ml MeOH and refluxed for 5 h. The solvent was evaporated and the residue purified by column chromatography with silica gel 60 and hexane/ethyl acetate 4:1. The products were obtained as colorless oils.

Methyl-3-oxodecanoate: 64%. Rf=0.6 (hexane/ethyl acetate 4:1). $^1$H-NMR (CDCl$_3$ 400.13 MHz) δ (ppm): 0.87 (m, 3H, —CH$_3$), 1.24-1.32 (m, 8H, —(CH$_2$)$_4$—CH$_3$), 1.59 (m, 2H, —CO—CH$_2$—CH$_2$—), 2.52 (t, 2H, J=7.4 Hz, —CO—CH$_2$CH$_2$—), 3.44 (5, 2H, COOMe-CH$_2$—CO—), 3.73 (s, 3H, —COOMe). $^{13}$C-NMR (CDCl$_3$ 100.62 MHz) δ (ppm): 14.1 (—CH$_3$), 22.6, 23.5, 28.9, 29.1, 31.7, 43.1 (—(CH$_2$)$_6$—CH$_3$), 49.0 (COOMe-CH$_2$—CO), 52.4 (—COOMe) 167.7 (—COOMe), 202.9 (—CO).

Methyl-3-oxododecanoate: 34%. Rf=0.65 (hexane/ethyl acetate 4:1). $^1$H-NMR (CDCl$_3$ 400.13 MHz) δ (ppm): 0.88 (m, 3H, —CH$_3$), 1.21-1.37 (m, 12H, —(CH$_2$)$_6$—CH$_3$), 1.63 (m, 2H, —CO—CH$_2$—CH$_2$—), 2.52 (t, 2H, J=7.4 Hz, —CO—CH$_2$—CH$_2$—), 3.44 (s, 2H, COOMe-CH$_2$—CO—), 3.74 (s, 3H, —COOMe). $^{13}$C-NMR (CDCl$_3$ 100.62 MHz) δ (ppm): 14.2 (—CH$_3$), 22.8, 23.6, 29.2, 29.4, 29.5, 29.5, 32.0, 43.2 (—(CH$_2$)$_8$—CH$_3$), 49.2 (COOMe-CH$_2$—CO), 52.4 (—COOMe) 167.8 (—COOMe), 203.0 (—CO).

General Synthesis of Methyl-3-Phenylamino-2-Enoates:

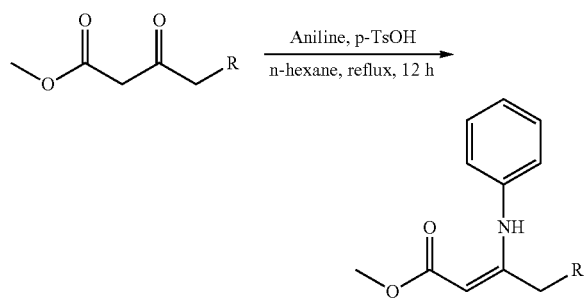

The β-keto-methyl ester was dissolved in 150 ml n-hexane with 1 eq, aniline and 2 mol % p-TsOH. 2 g molecular sieves 4 Å was added and the mixture refluxed for 12 h. After the reaction reach room temperature, the solvent was evaporated and the residue purified by column chromatography with silica gel 60 and hexane/ethyl acetate 9:1. The products were obtained as yellow oils.

Methyl (Z)-3-(phenylamino)dec-2-enoate: 69.5%. Rf=0.7 (hexane/ethyl acetate 9:1), $^1$H-NMR (CDCl$_3$ 400.13 MHz) δ (ppm): 0.84 (m, 3H, —CH$_3$), 1.09-1.30 (m, 8H, —(CH$_2$)$_4$—CH$_3$), 1.41 (m, 2H, =ON—CH$_2$—CH$_2$—), 2.29 (t, 2H, J=7.6 Hz, =CN—CH$_2$—CH$_2$—), 3.69 (s, 3H, —COOMe), 4.74 (s, 1H, COOMe-CH=CN—), 7.09 (m, 2H, Ar), 7.17 (m, 1H, Ar), 7.33 (m, 2H, Ar), 10.29 (s, 1H, —NH—). $^{13}$C-NMR (CDCl$_3$ 100.62 MHz) δ (ppm): 13.8 (—CH$_3$), 22.3, 27.8, 28.6, 28.8, 31.3, 32.0 (—(CH$_2$)$_6$—CH$_3$), 50.1 (COOMe), 84.3 (COOMe-CH=CN—), 124.9 (20, Ar), 125.0 (Ar), 128.8 (20, Ar), 139.1 (Ar), 163.6 (=CN—), 170.8 (COOMe).

Methyl (Z)-3-(phenylamino)dodec-2-enoate: 52%. Rf=0.75 (hexane/ethyl acetate 9:1). $^1$H-NMR (CDCl$_3$ 400.13 MHz) δ (ppm): 0.87 (m, 3H, —CH$_3$), 1.12-1.31 (m, 12H, —(CH$_2$)$_6$—CH$_3$), 1.41 (m, 2H, =CN—CH$_2$—CH$_2$—), 2.28 (m, 2H, =CN—CH$_2$—CH$_2$—), 3.69 (s, 3H, —COOMe), 4.73 (s, 1H, COOMe-CH=CN—), 7.09 (m, 2H, Ar), 7.17 (m, 1H, Ar), 7.32 (m, 2H, Ar), 10.29 (s, 1H, —NH—). $^{13}$C-NMR (CDCl$_3$ 100.62 MHz) δ (ppm): 14.2 (—CH$_3$), 22.7, 28.1, 29.2, 29.27, 29.34, 29.5, 32.0, 32.4 (—(CH$_2$)$_8$—CH$_3$), 50.4 (COOMe), 84.7 (COOMe-CH=CN—), 125.2 (2C, Ar), 125.4 (Ar), 129.2 (20, Ar), 139.4 (Ar), 163.9 (=CN—), 171.1 (COOMe).

General Synthesis of Quinolin-4-Ones (Compounds Represented by the Formulas (2) and (4)):

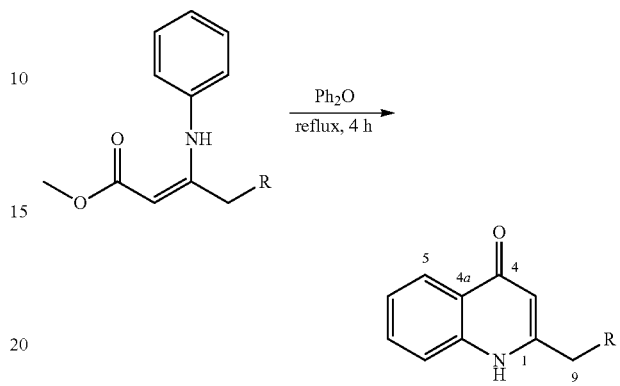

The methyl-3-phenylamino-2-enoate was dissolved in diphenyl ether (10 ml/1 g educt) and refluxed for 4 h. The reaction mixture was allowed to cool and dropwise added to n-hexane. The precipitate was filtered and washed with n-hexane. The products were obtained as white solids.

2-Heptylquinolin-4-one (2): 81%. $^1$H-NMR (DMSO-d$_6$ 400.13 MHz) δ (ppm): 0.86 (m, 3H, H-15), 1.20-1.37 (m, 6H, H-12-14), 1.67 (m, 2H, H-10), 2.58 (t, 2H, J=7.4 Hz, H-9), 5.91 (s, 1H, H-3), 7.26 (m, 1H, H-6), 7.51 (d, 1H, J=8.1 Hz, H-8), 7.60 (m, 1H, H-7), 8.03 (dd, 1H, J=8.1 Hz, J=1.2 Hz, H-5), 11.43 (s, 1H, NH). $^{13}$C-NMR (DMSO-d$_6$ 100.62 MHz) δ (ppm): 13.9 (C-15), 22.0, 28.3 (20), 28.4, 31.1 (C-10-14), 33.2 (0-9), 107.6 (C-3), 117.8 (C-8), 122.6 (C-6), 124.6 (C-4a), 124.7 (C-5), 131.4 (C-7), 140.1 (C-8a), 153.8 (C-2), 176.8 (C-4). TOF-HRMS: m/z=244.1693 [M+H]$^+$, calc. for C$_{16}$H$_{21}$NO+H$^+$=244.1701; 487.3303 [2M+H]$^+$, calc. for C$_{32}$H$_{42}$N$_2$O$_2$+H$^+$=487.3325.

2-Nonylquinolin-4-one (4): 83%. $^1$H-NMR (DMSO-d$_6$ 400.13 MHz) δ (ppm): 0.84 (m, 3H, H-17), 1.18-1.36 (m, 12H, H-11-16), 1.66 (m, 2H, H-10), 2.57 (t, 2H, J=7.4 Hz, H-9), 5.91 (s, 1H, H-3), 7.26 (m, 1H, H-6), 7.52 (d, 1H, J=8.1 Hz, H-8), 7.60 (m, 1H H-7), 8.03 (dd, 1H, J=8.1 Hz, J=1.0 Hz, H-5), 11.43 (5, 1H, NH). $^{13}$C-NMR (DMSO-d$_6$ 100.62 MHz) δ (ppm): 13.9 (C-17), 22.0, 28.3, 28.4, 28.6, 28.7, 28.8, 31.2 (C-10-16), 33.2 (C-9), 107.6 (C-3), 117.8 (C-8), 122.6 (C-6), 124.6 (C-4a), 124.7 (C-5), 131.4 (C-7), 140.1 (C-8a); 153.5 (C-2), 176.8 (C-4). TOF-HRMS: m/z=272.2003 [M+H]$^+$, calc. for C$_{18}$H$_{25}$NO+H$^+$=272.2014; 543.3971 [2M+H]$^+$, calc. for C$_{36}$H$_{50}$N$_2$O$_2$H$^+$=543.3951.

General Synthesis of Ethyl Carbonates:

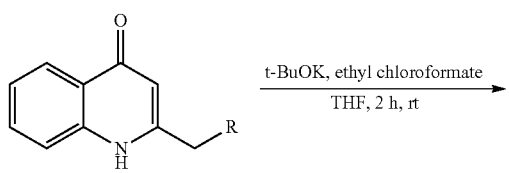

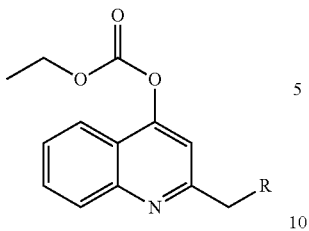

2-Alkyl-4-quinolones were dissolved in THF (10 ml/0.4 g 2-Alkyl-4-quinolones) together with 1.25 eq. t-BuOK. The reaction was stirred at room temperature for 1 h. Ethyl chloroformate (2.15 eq.) was added and the mixture was stirred at room temperature for 1 h. The reaction was quenched by the addition of $H_2O$ and the THF was evaporated under reduced pressure. The residue was diluted with $H_2O$ and extracted with ethyl acetate: The combined organic phases were dried with $MgSO_4$, filtered and evaporated to yield the pure compound. If traces of educt or byproducts were visible on TLC, the residue was purified by column chromatography on silica gel using petrol ether/ethyl acetate 7:3, The products were received as slightly yellow oils.

Ethyl (2-heptylquinolin-4-yl) carbonate: 96%. Rf=0.8 (petrol ether/ethyl acetate 7:3). $^1$H-NMR (CDCl$_3$ 399.79 MHz) δ (ppm): 0.87 (m, 3H, H-15), 1.23-1.48 (m, 8H, H-11-14), 1.45 (t, J=7.2 Hz, 3H, CH$_3$—CH$_2$—O), 1.82 (m, 2H, H-10), 2.97 (m, 2H, H-9), 4.40 (q, J=7.0 Hz, 2H, CH$_3$—CH$_2$—O), 7.31 (5, 1H, H-3), 7.51 (m, 1H, H-6); 7.71 (m, 1H, H-7), 7.99 (d, J=8.5 Hz, 1H, H-5), 8.06 (d, J=8.5 Hz, 1H, H-8). $^{13}$C-NMR (CDCl$_3$ 100.52 MHz) δ (ppm): 14.2 (C-15), 14.3 (CH$_3$—CH$_2$—O), 22.8, 29.3, 29.6, 31.9 (C-11, C-12, C-13, C-14), 30.0 (C-10), 39.7 (C-9), 65.6 (CH$_3$—CH$_2$—O), 112.0 (C-3), 120.6 (0-4a), 121.1 (C-5), 126.2 (C-6), 128.9 (C-8), 130.2 (C-7), 149.6 (C-8a), 152.5 (—OCOO), 154.5 (C-4), 164.2 (C-2).

Ethyl (2-nonylquinolin-4-yl) carbonate: 95%. Rf=0.9 (petrol ether/ethyl acetate 7:3). $^1$H-NMR (CDCl$_3$ 399.79 MHz) δ (ppm): 0.87 (m, 3H, H-17), 1.24-1.47 (m, 12H, H-11-16), 1.44 (t, J=7.2 Hz, 3H, CH$_3$—CH$_2$—O), 1.81 (m, 2H, H-10), 2.97 (m, 2H, H-9), 4.40 (q, J=7.0 Hz, 2H, CH$_3$—CH$_2$—O), 7.31 (s, 1H, H-3), 7.50 (m, 1H, H-6), 7.70 (m, 1H, H-7), 7.99 (d, J=8.5 Hz, 1H, H-5), 8.06 (d, J=8.5 Hz, 1H, H-8). $^{13}$C-NMR (CDCl$_3$ 100.52 MHz) δ (ppm): 14.2 (C-17), 14.3 (CH$_3$—CH$_2$—O), 22.8, 29.4, 29.61 (2C), 29.64, 29.9, 32.0 (C-10-16), 39.7 (C-9), 65.6 (CH$_3$—CH$_2$—O), 112.0 (C-3), 120.6 (C-4a), 121.1 (C-5), 126.2 (C-6), 129.0 (C-8), 130.1 (C-7), 149.6 (C-8a), 152.5 (—OCOO), 154.4 (C-4), 164.2 (C-2).

General Synthesis of Ethyl Carbonate N-Oxides:

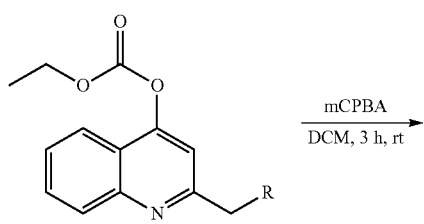

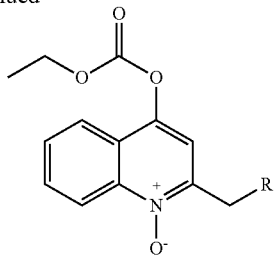

Ethyl carbonates were dissolved in DCM (10 ml/250 mg) together with 1.1 eq. mCPBA. The reaction was stirred at room temperature for 3 h. The solution was washed twice with aqueous 0.5 M $Na_2CO_3$ solution and once with $H_2O$. The organic phases were dried with $MgSO_4$, filtered and evaporated. The residue was purified by column chromatography on silica gel using ethyl acetate. The products were received as colorless oils.

4-((Ethoxycarbonyl)oxy)-2-heptylquinoline 1-oxide: 86%. Rf=0.6 (ethyl acetate). $^1$H-NMR (CDCl$_3$ 399.79 MHz) δ (ppm): 0.87 (m, 3H, H-15), 1.25-1.51 (m, 8H, H-11-14), 1.43 (t, J=7.2 Hz, 3H, CH$_3$—CH$_L$-0), 1.81 (m, 2H, H-10), 3.12 (m, 2H, H-9), 4.39 (q, J=7.2 Hz, 2H, CH$_3$—CH$_2$—O), 7.34 (s, 1H, H-3), 7.62 (m, 1H, H-6), 7.78 (m, 1H, H-7), 7.98 (d, J=8.5 Hz, 1H, H-5), 8.78 (d, J=8.8 Hz, 1H, H-8). $^{13}$C-NMR (CDCl$_3$100.52 MHz) δ (ppm): 14.2 (C-15), 14.3 (CH$_3$-0H$_2$—O), 26.1 (C-10), 22.7, 29.2, 29.7 (C-11-14), 31.83 (C-11-14 or C-9), 31.85 (C-11-14 or 0-9), 65.9 (CH$_3$—CH$_2$—O), 113.4 (C-3), 120.3 (C-8), 121.9 (C-5), 122.7 (C-4a), 128.2 (C-6), 131.0 (C-7), 142.4 (C-8a), 143.8 (C-4), 149.7 (C-2), 152.5 (—OCOO).

4-((Ethoxycarbonyl)oxy)-2-nonylquinoline 1-oxide: 89%. Rf=0.7 (ethyl acetate). $^1$H-NMR (CDCl$_3$ 399.79 MHz) δ (ppm): 0.87 (m, 3H, H-17), 1.22-1.52 (m, 12H, H-11-16), 1.45 (t, J=7.2 Hz, 3H, CH$_3$—CH$_2$—O), 1.82 (m, 2H, H-10), 3.13 (m, 2H, H-9), 4.40 (q, J=7.2 Hz, 2H, CH$_3$—CH$_2$—O), 7.35 (s, 1H, H-3), 7.63 (m, 1H, H-6), 7.79 (m, 1H, H-7), 8.00 (d, J=8.5 Hz, 1H, H-5), 8.79 (d, J=8.8 Hz, 1H, H-8). $^{13}$C-NMR (CDCl$_3$ 100.52 MHz) δ (ppm): 14.2 (C-17), 14.3 (CH$_3$—CH$_2$—O), 26.2 (C-10), 22.8, 29.4, 29.5, 29.6, 29.7, 31.9, 32.0 (C-9, C-11-16), 65.9 (CH$_3$—CH$_2$—O), 113.4 (C-3), 120.3 (C-8), 122.0 (C-5), 122.7 (C-4a), 128.2 (C-6), 131.1 (C-7), 142.5 (C-8a), 144.0 (C-4), 149.9 (C-2), 152.5 (—OCOO), General Synthesis of 1-Hydroxy-Chinolin-4-Ones (Compounds Represented by the Formulas (3) and (5)):

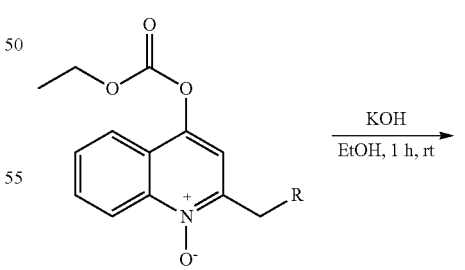

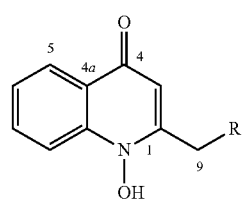

Ethyl-carbonate-N-oxides were dissolved in EtOH (10 ml 1300 mg) and 17 eq. aqueous 5 M KOH solution was added. The reaction became yellow and was stirred at room temperature for 1 h. H$_2$O was added and the pH adjusted to 1-2 with conc. HCl, whereupon a milky suspension formed which soon crystallized. The product was collected by filtration and washed with H$_2$O. The product was received as a white crystalline solid.

1-Hydroxy-2-heptylquinolin-4(1H)-one (3): 74.5%. $^1$H-NMR (MeOD-d$_4$ 399.79 MHz) δ (ppm): 0.91 (m, 3H, H-15), 1.27-1.51 (m, 8H, H-11-14), 1.78 (m, 2H, H-10), 2.93 (m, 2H, H-9), 6.34 (s, 1H, H-3), 7.51 (m, 1H, H-6), 7.81 (m, 1H, H-7), 8.09 (d, J=8.6 Hz, 1H, H-8), 8.26 (d, J=8.2 Hz, 1H, H-5). $^{13}$C-NMR (MeOD-d$_4$ 100.52 MHz) δ (ppm): 14.4 (C-15), 28.9 (C-10), 23.7, 30.1, 30.4, 32.9 (C-11-14), 32.5 (C-9), 107.5 (C-3), 116.8 (C-8), 125.3 (C-4a), 125.9 (C-5), 126.0 (C-6), 133.7 (C-7), 142.0 (C-8a), 156.4 (C-2), 174.0 (C-4, only in HMBC). TOF-HRMS: m/z=260.1638 [M+H]$^+$, calc. for C$_{16}$H$_{21}$NO$_2$+H$^+$=260.1651; 519.3199 [2M+H]$^+$, calc. for C$_{32}$H$_{42}$N$_2$O$_4$+H$^+$=519.3223.

1-Hydroxy-2-nonylquinolin-4(1H)-one (5): 87%. $^1$H-NMR (MeOD-d$_4$ 399.79 MHz) δ (ppm): 0.90 (m, 3H, H-17), 1.24-1.51 (m, 12H, H-11-16), 1.79 (m, 2H, H-10), 2.93 (m, 2H, H-9), 6.34 (s, 1H, H-3), 7.51 (m, 1H, H-6), 7.82 (m, 1H, H-7), 8.09 (d, J=8.6 Hz, 1H, H-8), 8.26 (d, J=8.2 Hz, 1H, H-5). $^{13}$C-NMR (MeOD-d$_4$ 100.95 MHz) δ (ppm): 14.4 (C-17), 28.9 (C-10), 23.7, 30.4 (3C), 30.6, 33.0 (C-11-16), 32.6 (C-9), 107.5 (0-3), 116.8 (C-8), 125.3 (C-4a), 125.9 (C-5), 126.1 (C-6) 133.7 (C-7), 142.0 (C-8a), 156.5 (C-2), 173.9 (C-4, only in HMBC). TOF-HRMS: m/z=288.1951 [M+H]$^+$, calc. for C$_{18}$H$_{25}$NO$_2$+H$^+$=288.1964; 575.3833 [2M+H]', calc. for C$_{36}$H$_{50}$N$_2$O$_4$+H$^+$=575.3849.

Synthesis of Trans-Δ$^1$-NQ and Trans-Δ$^1$-NQNO (Compounds Represented by the Formulas (6) and (7))

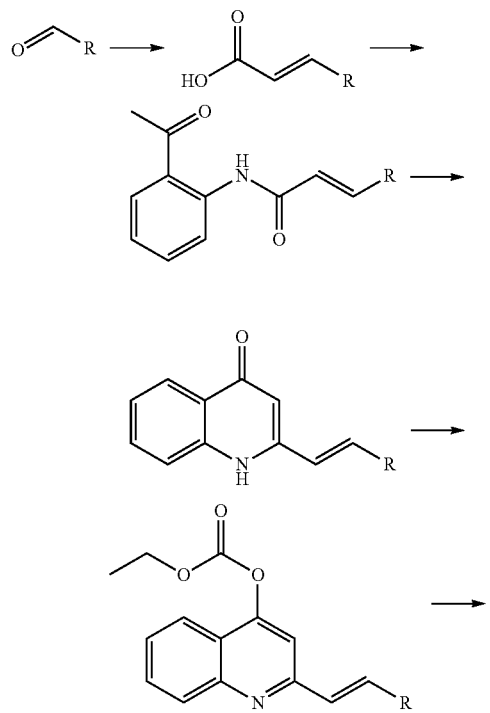

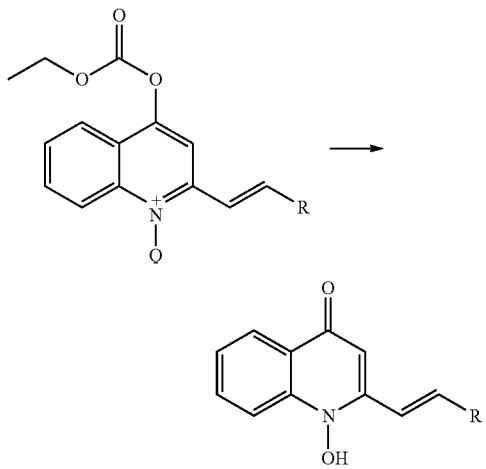

R = C$_7$H$_{15}$

Synthesis of (E)-Dec-2-Enoic Acid:

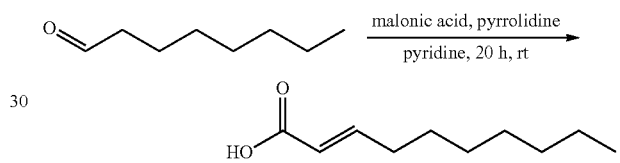

Malonic acid (2.5 g, 24 mmol) was dissolved in 10 ml dry pyridine and 3.75 ml octanal (24 mmol) and 250 µl pyrrolidine was added. The mixture warmed up and the development of gas was observed. The mixture was stirred at room temperatures for 20 h and was then poured in ice water and acidified with conc. HCl. The mixture was extracted with ethyl acetate and the combined organic phases washed with brine, dried with MgSO$_4$, filtered and the solvent was evaporated. The product was purified by column chromatography using petrol ether/ethyl acetate 5:1. The product was obtained as colorless oil (m=2.97 mg, 72.7%). Rf=0.175 (ether/ethyl acetate 5:1). $^1$H-NMR (CDCl$_3$ 399.79 MHz) δ (ppm): 0.89 (m, 3H, —CH$_2$CH$_3$), 1.18-1.39 (m, 12H, —(CH$_2$)$_4$—CH$_3$), 1.47 (m, 2H, —CH$_2$—(CH$_2$)$_4$—CH$_3$), 2.23 (m, 1H, =CH—CH$_2$—), 5.82 (dt, J=15.6 Hz, J=1.5 Hz, 1H, HOOC—CH=), 7.08 (dt, J=15.6 Hz, J=7.08 Hz, 1H, =CH—CH$_2$—). $^{13}$C-NMR (CDCl$_3$ 100.53 MHz) δ (ppm): 14.2 (—CH$_2$—CH$_3$), 22.8, 29.18, 29.25, 31.9 (—(CH$_2$)$_4$—CH$_3$), 28.0 (—CH$_2$—(CH$_2$)$_4$—CH$_3$), 32.5 (=CH—CH$_2$—), 120.6 (HOOC—CH=), 152.6 (=CH—CH$_2$—), 171.7 (HOOC—).

Synthesis of (E)-N-(2-Acetylphenyl)Dec-2-Enamide:

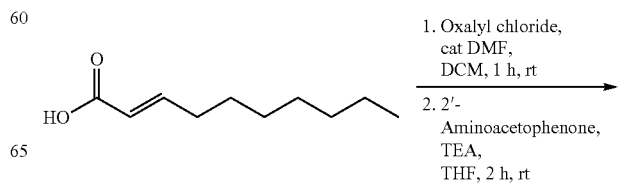

1. Oxalyl chloride, cat DMF, DCM, 1 h, rt
2. 2'-Aminoacetophenone, TEA, THF, 2 h, rt

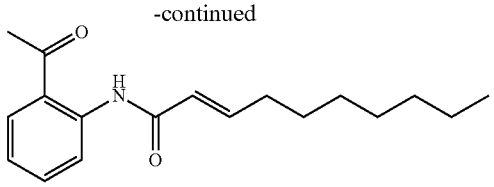

2-Decenoic acid (1.0 g, 5.875 mmol) was dissolved in 22 ml dry DCM and 5.9 ml oxalyl chloride (2M in DCM, 11.8 mmol) was added. Three drops of DMF were added and the reaction stirred at room temperature for 1 h. The solvent was evaporated under reduced pressure. The residue dissolved in 13 ml dry THF and added to a stirring mixture of 715 μl 2'-Aminoacetophenone (5.875 mmol) and 820 μl TEA (5.875 mmol) in 18 ml dry THF at room temperature. The mixture was stirred at room temperature for 2 h in which a large amount of precipitate was observed and the color changed to yellow. Water was added and extracted with DCM. The combined organic phases were washed with brine, dried with MgSO$_4$, filtered and the solvent was evaporated. The residue was purified by column chromatography on silica 60 with DCM/petrol ether 2:1. The product was obtained as yellow oil (m=827 mg, 49%). Rf=0.4 (DCM/petrol ether 2:1). Rf=0.4 (DCM/petrol ether 2:1). $^1$H-NMR (CDCl$_3$ 400.13 MHz) δ (ppm): 0.89 (m, 3H, —CH$_2$—CH$_3$), 1.23-1.38 (m, 8H, —(CH$_2$)$_4$—CH$_3$), 1.50 (m, 2H, —CH=CH—CH$_2$—CH$_2$—), 2.25 (m, 2H, —CH=CH—CH$_2$—CH$_2$—), 2.67 (s, 3H, —CO—CH$_3$), 5.99 (dt, 1H, J=15.4 Hz, J=1.5 Hz, —CH=CH—CH$_2$—), 6.98 (dt, 1H, J=15.4 Hz, J=7.0 Hz, —CH=CH—CH$_2$—), 7.11 (m, 1H, H-4), 7.56 (m, 1H, H-5), 7.90 (dd, 1H, J=8.0 Hz, J=1.4 Hz, H-3), 8.85 (dd, 1H, J=8.6 Hz, J=0.8 Hz, H-6), 11.82 (s, 1H, —NH). $^{13}$C-NMR (CDCl$_3$ 100.62 MHz) δ (ppm): 14.2 (—CH$_3$), 22.8, 29.2, 29.3, 31.9 (—(CH$_2$)$_4$—CH$_3$), 28.4 (—CH=CH—CH$_2$—CH$_2$—), 28.7 (—CO—CH$_3$), 32.4 (—CH=CH—CH$_2$—CH$_2$—), 121.1 (C-6), 121.9 (C-2), 122.3 (C-4), 125.4 (—CH=CH—CH$_2$—), 131.8 (C-3), 135.3 (C-5), 141.6 (C-1), 146.6 (—CH=CH—CH$_2$—), 165.3 (NH—CO—), 203.0 (—CO—CH$_3$).

Synthesis (E)-2-(Non-1-En-1-Yl)Quinolin-4-One (Compound Represented by the Formula (6)):

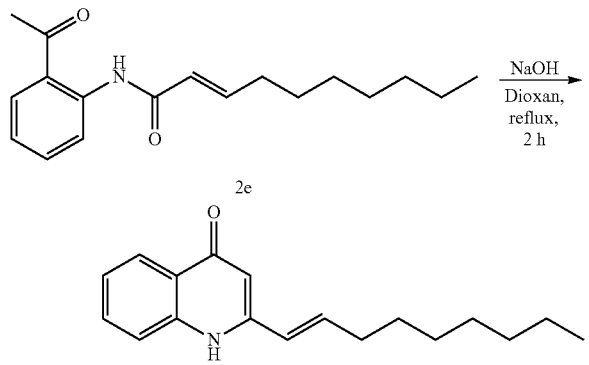

The amide 2e (170 mg, 0.59 mmol) and 80 mg crushed NaOH (2 mmol) were dissolved in 20 ml dry 1,4-dioxan and refluxed for 2 h. The reaction was cooled to room temperature and the solvent evaporated under reduced pressure. To the residue was added 10 ml water and 100 ml n-hexane and the mixture sonicated for 2 min. The aqueous phase was neutralized with 1 M HCl and saturated NaHCO$_3$ and the precipitate collected by filtration. The filter cake was washed with hexane and dissolved in ethanol. The ethanol was evaporated and 10 ml ethyl acetate was added to the residue. The white precipitate was collected by filtration, washed with 5 ml ethyl acetate and dried under vacuum. The pure product was obtained as white solid (m=93 mg, 58.5%). $^1$H-NMR (DMSO-d$_6$ 399.79 MHz) δ (ppm): 0.87 (m, 3H, H-17), 1.23-1.37 (m, 8H, H-13-16), 1.48 (m, 2H, H-12), 2.26 (m, H-11), 6.12 (s, 1H, H-3), 6.30 (dt, 1H, J=16.0 Hz, J=1.1 Hz, H-9), 6.78 (dt, 1H, J=16.0 Hz, J=6.8 Hz, H-10), 7.26 (m, 1H, H-6), 7.58-7.65 (m, 2H, H-7 and H-8), 8.02 (m, 1H, H-5), 11.34 (s, br, 1H, —NH). $^{13}$C-NMR (DMSO-d$_6$ 100.52 MHz) δ (ppm): 13.9 (C-17), 22.0, 28.46, 28.51, 31.2 (C-13-16), 28.1 (C-12), 32.3 (C-11), 106.1 (C-3), 118.3 (C-8), 122.7 (C-6), 124.1 (C-9), 124.6 (C-5), 125.0 (C-4a), 131.5 (C-7), 138.6 (C-10), 140.3 (C-8a), 147.2 (C-2), 176.8 (C-4). TOF-HRMS: m/z=270.1846 [M+H]$^+$, calc. for C$_{18}$H$_{23}$NO+H$^+$=270.1858; 539.3613 [2M+H]$^+$, calc. for C$_{36}$H$_{46}$N$_2$O$_2$+H$^+$=539.3638.

Synthesis of (E)-Ethyl (2-(Non-1-En-1-Yl)Quinolin-4-Yl) Carbonate:

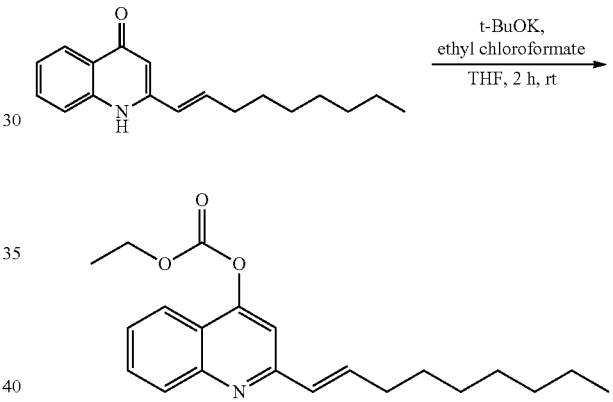

trans-Δ$^1$ NQ (366 mg, 1.36 mmol) was dissolved in 10 ml THF by the addition of 191 mg t-BuOK (1.7 mmol, 1.25 eq.). The mixture was stirred for 1 h at room temperature. Ethyl chloroformate (280 μl, 2.92 mmol, 2.15 eq.) was added and the mixture stirred for 1 h at room temperature. The reaction was quenched by the addition of H$_2$O and the THF evaporated under reduced pressure. The residue was diluted with H$_2$O and extracted with ethyl acetate. The combined organic phases were dried with MgSO$_4$, filtered and evaporated to yield the pure compound as colorless oil (460 mg, 99%). Rf=0.78 (petrol ether/ethyl acetate 7:3). $^1$H-NMR (CDCl$_3$ 399.79 MHz) δ (ppm): 0.89 (m, 3H, H-17), 1.25-1.39 (m, 8H, H-13-16), 1.44 (t, J=7.2 Hz, 3H, CH$_3$—CH$_2$—O), 1.54 (m, 2H, H-12), 2.32 (m, 2H, H-11), 4.40 (q, J=7.2 Hz, 2H, CH$_3$—CH$_2$—O), 6.70 (dt, 1H, J=15.9 Hz, J=0.9 Hz, —CH=CH—CH$_2$—), 6.82 (dt, 1H, J=15.9 Hz, J=6.7 Hz, —CH=CH—CH$_2$—), 7.49 (m, 1H, H-6), 7.52 (s, 1H, H-3), 7.70 (m, 1H, H-7), 7.96 (m, 1H, H-5), 8.05 (m, 1H, H-8). $^{13}$C-NMR (CDCl$_3$ 100.52 MHz) δ (ppm): 14.2 (C-17), 14.3 (CH$_3$—CH$_2$—O), 22.8, 29.3, 29.4, 31.9 (C-13-16), 29.0 (C-12), 33.2 (C-11), 65.6 (CH$_3$—CH$_2$—O), 109.4 (C-3), 121.0 (C-4a), 121.1 (C-5), 126.4 (C-6), 129.2 (C-8), 130.4 (C-7), 130.8 (C-9) 139.2 (C-10), 149.8 (C-8a), 152.7 (—OCOO) 154.6 (C-4) 157.7 (C-2).

Synthesis of (E)-4-((Ethoxycarbonyl)Oxy)-2-(Non-1-En-1-Yl)Quinoline 1-Oxide:

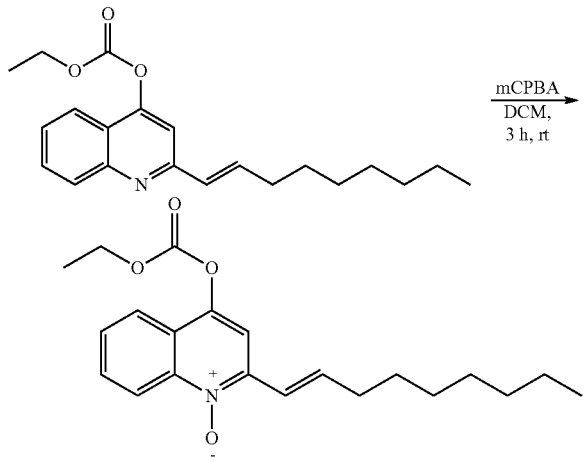

Protected trans-Δ¹ NQ (460 mg, 1.35 mmol) was dissolved in 20 ml DOM and 330 mg mCPBA (77%, 1.1 eq.) was added. The mixture was stirred for 3 h at room temperature. The solution was washed twice with aqueous 0.5 M $Na_2CO_3$ solution and once with $H_2O$. The organic phases were dried with $MgSO_4$, filtered and evaporated. The residue was purified by column chromatography on silica gel using petrol ether/ethyl acetate (1:1). The product was collected as second of two fractions as yellow oil (405 mg, 84%). Rf=0.45 (PE/EE 1:1). ¹H-NMR (CDCl₃ 399.79 MHz) δ (ppm): 0.88 (m, 3H, H-17), 1.26-1.41 (m, 8H, H-13-16), 1.44 (t, J=7.2 Hz, 3H, $CH_3$—$CH_2$—O), 1.54 (m, 2H, H-12), 2.38 (m, 2H, H-11), 4.40 (q, J=7.2 Hz, 2H, $CH_3$-0$H_2$-0), 6.79 (dt, 1H, J=16.2 Hz, J=7.1 Hz, —CH═CH—$CH_2$—), 7.37 (dt, 1H, J=16.2 Hz, J=1.5 Hz, —CH═CH—$CH_2$—), 7.55 (s, 1H, H-3), 7.61 (m, 1H, H-6), 7.77 (m, 1H, H-7), 7.95 (d, J=8.3 Hz, 1H, H-5), 8.78 (d, J=8.7 Hz, 1H, H-8). ¹³C-NMR (CDCl₃100.52 MHz) (ppm): 14.2 (C-17), 14.3 ($CH_3$-0$H_2$—O), 28.9 (C-12), 22.8, 29.3, 29.4, 31.9 (C-13-16), 33.9 (C-11), 65.9 ($CH_3$—$CH_2$—O), 110.5 (C-3), 120.7 (C-8), 121.8 (C-9), 121.9 (C-5), 122.8 (C-4a), 128.4 (C-6), 131.1 (C-7), 142.0 (C-10), 142.6 (C-8a), 143.8 (C-4), 144.4 (C-2), 152.6 (—OCOO).

Synthesis of (E)-1-Hydroxy-2-(Non-1-En-1-Yl)Quinolin-4-One (Compound Represented by the Formula (7)):

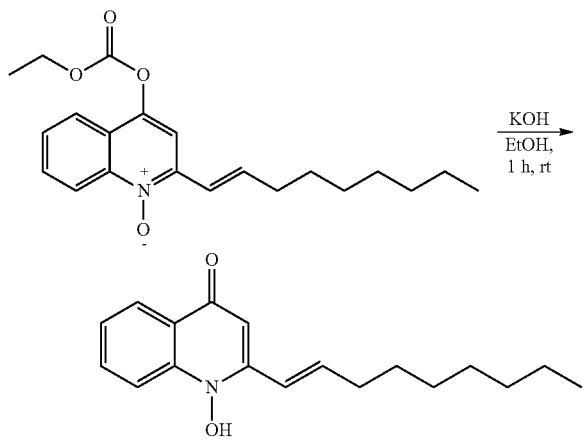

Protected trans-Δ¹ NQNO (342 mg, 0.957 mmol) was dissolved in 10 ml ethanol and 3 ml aqueous 5 M KOH solution was added. The reaction turned yellow and was stirred at room temperature for 1 h. $H_2O$ was added and the pH adjusted to 1-2 with conc. HCl, whereupon a milky suspension formed which soon crystallized. The product was collected by filtration and washed with $H_2O$. The product was received as a yellow solid (230 mg, 84%). ¹H-NMR (MeOD-d₄ 399.79 MHz) δ (ppm): 0.92 (m, 3H, H-17), 1.29-1.46 (m, 8H, H-13-16), 1.57 (m, 2H, H-12), 2.38 (m, 2H, H-11), 6.71 (s, 1H, H-3), 6.80 (dt, 1H, J=16.0 Hz, J=6.9 Hz, —CH═CH—$CH_2$—), 7.04 (dt, 1H, J=16.0 Hz, J=1.6 Hz, —CH═CH—$CH_2$—), 7.55 (m, 1H, H-6), 7.83 (m, 1H, H-7), 8.21 (d, J=8.7 Hz, 1H, H-8), 8.26 (dd, J=8.2 Hz, J=1.4 Hz, 1H, H-5). ¹³C-NMR (MeOD-d₄ 100.53 MHz) δ (ppm): 14.4 (C-17), 23.7, 30.2, 30.3, 33.0 (C-13-16), 29.7 (C-12), 34.5 (C-11), 103.2 (C-3), 117.7 (C-8), 121.5 (C-9), 125.0 (C-4a), 125.5 (C-5), 126.7 (C-6), 133.7 (C-7), 141.8 (C-8a), 144.6 (C-10), 150.6 (C-2), 169.7 (C-4, only in HMBC). TOF-HRMS: m/z=286.1794 [M+H]⁺, calc. for $C_{18}H_{23}NO_2H^+$=286.1807; 571.3514 [2M+H]⁺, calc. for $C_{36}H_{46}N_2O4H^+$=571.3536.

Example 1: Determination of the Inhibitory Effect of NQNO (Compound Represented by the Formula (5)) Against *Neisseria gonorrhoeae, Neisseria Macacae*, and *Lactobacillus brevis* by Measuring Growth Curves in Comparison to a DMSO Treated Control Growth experiments with NQNO were conducted against *Neisseria gonorrhoeae* strain MS11 (Edwards, M., et al., Antigenic analysis of gonococcal pili using monoclonal antibodies, J Exp Med, 1984. 160(6): p. 1782-91) and a multidrug-resistant *N. gonorrhoeae* isolate from Slovenia (Unemo M, Golparian O, Potočnik M, Jeverica S. Treatment failure of pharyngeal gonorrhoea with internationally recommended first-line ceftriaxone verified in Slovenia, September 2011. Euro Surveill. 2012; 17(25):pii=20200), *Neisseria macacae*, and *Lactobacillus brevis*. The bacteria were inoculated in GC (Difco™ GC medium Ref. 228950, BD Becton Dickinson) and PPM broth (15 g/L Proteon Pepton, 1 g/L soluble starch, 5 g/L NaCl, 4 g/L $KH_2PO_4$, 1 g/L $K_2HPO_4$, pH 7.5) (Neisseriae) or TSB (BBL™ Trypticase Soy Broth Ref 211768, BD Becton Dickinson) (*Lactobacillus*) supplemented with solvent (DMSO) or the indicated concentrations of NQNO (5-50 04) and their growth at 37° C. was monitored over the course of 10 h by optical density readings in 30 minute intervals.

In particular, the growth of the bacteria in this and the following Examples (if not stated otherwise) has been conducted as follows:

*Neisseria* strains were cultured in PPM medium (15 g/l Proteon Pepton, 1 g/l soluble starch, 5 g/l NaCl, 4 g/l $KH_2PO_4$, 1 g/l $K_2HPO_4$, pH 7.5) for liquid culture and on GC plates (BD Difco™ GC Medium Base) supplemented with 1% vitamin mix (100 g/l glucose, 10 WI glutamine, 26 g/l L-cystein, 100 mg/l carboxylase, 250 mg/l NAD, 500 μl Fe(NO₃)₃, 150 mg/l arginine, 3 mg/l thiamine-HCl, 10 mg/l vitamine B12, 13 mg/I p-amino benzoic acid, 1.1 g/l L-cystin, 1 g/l adenine; 500 mg/l uracil, 30 mg/I guanine). Strains were either cultivated at 37° C. and 220 rpm (liquid medium) or at 37° C. and 5% $CO_2$ (solid medium).

*Haemophilus influenzae* was grown in BHI medium (BD Difco Brain Heart Infusion) supplemented with 20 μg/ml Haemin, 20 μg/ml NAD and 15 g/l agar for plates. *Escherichia coli* strains, *Pseudomonas aeruginosa* and *Klebsiella*

*pneumoniae* were cultured in LB medium (10 WI tryptone, 5 g/l yeast extract, 5 g/l NaCl, 15 g/l agar for plates; pH 7.0). *P. aeruginosa* PAO1 mutants were obtained from Cohn Manoil (University of Washington, Genome Sciences, Seattle, Wash.).

*Lactobacillus* strains were grown in TSB medium as stated above or in 5 ml PYG medium (5 g/l trypticase peptone, 5 WI peptone, 10 g/l yeast extract, 5 WI beef extract; 5 g/l glucose; 2 g/l $K_2HPO_4$, 1 ml/l Tween 80, 0.5 g/l cysteine-HClx$H_2O$, 1 mg/l resazurin, 40 ml/l salt solution (0.25 g/l $CaCl_2$×2 $H_2O$, 0.5 g/l $MgSO_4$×7 $H_2O$, 1 g/l $K_2HPO_4$, 1 WI $KH_2PO_4$, 10 WI $NaHCO_3$, 2 WI NaCl in MiliQ), 10 ml/l haemin solution (500 mg/l haemin, 10 ml/l 1N NaOH in Milk)), 0.2 mill vitamin K1 solution (5 ml/l vitamin K1 in 95% ethanol), 950 ml/l distilled water, pH 7.2) overnight at 30° C. at 200 rpm.

For *Candida albicans* cultivation YPG medium (10 g/l yeast extract; 20 g/l peptone, 20 WI glucose in MiliQ) was used. The yeast was incubated overnight at 30° C. and 100 rpm.

Before every experiment, bacteria were pre-cultured in 5 ml liquid medium for at least 2 hours then harvested and resuspended in PBS (phosphate buffered saline). Optical density (OD) was determined and a volume equal to an OD of 0.2 was inoculated into 5 ml of the respective medium. NQNO was added at the indicated amounts (5-50 μM). DMSO level was adjusted to 1% of final concentration. Samples were incubated for either 10.5 hours, until they reached stationary phase (three measured values in stationary phase) or until they reached an OD of 2.5. Optical density was determined every 0.5 h.

Figure 2:
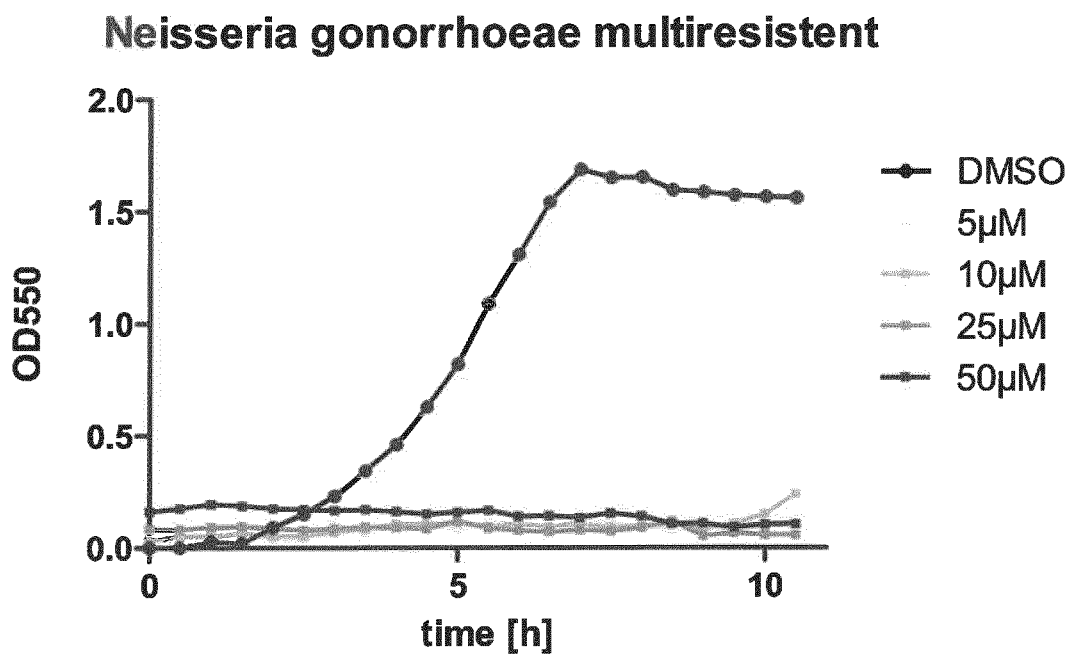
FIG. 2: Growth curves of *Neisseria gonorrhoeae* multi-resistent in the presence of different concentrations of NQNO (control: treatment with DMSO).
Figure 3:
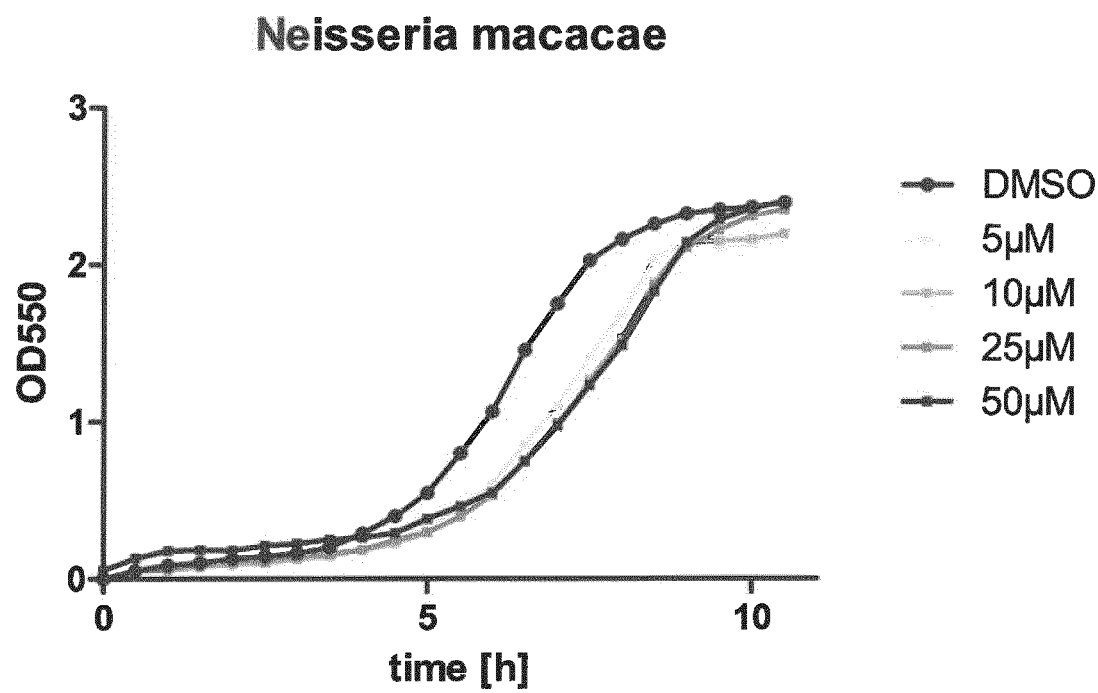
FIG. 3: Growth curves of *Neisseria macacae* in the presence of different concentrations of NQNO (control: treatment with DMSO).
Figure 4:
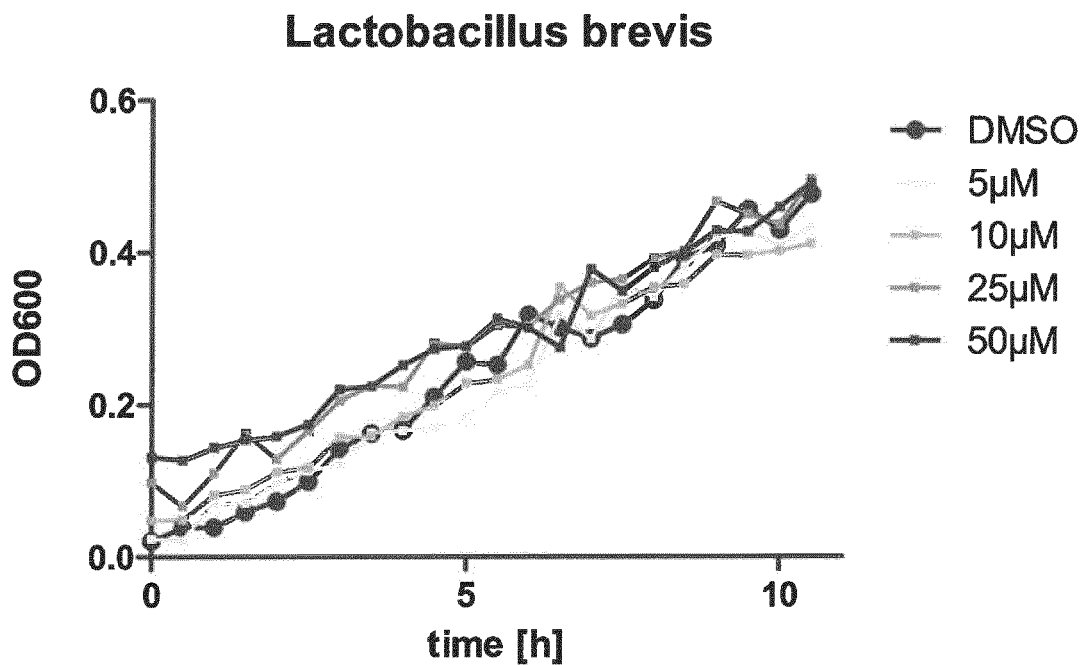
FIG. 4: Growth curves of *Lactobacillus brevis* in the presence of different concentrations of NQNO (control: treatment with DMSO).

The growth experiments with NQNO demonstrated that said compound is an extremely potent antibiotic against the gram-negative pathogen *N. gonorrhoeae*. Concentrations as low as 5 μM (<1.4 μg/mL) led to a complete abrogation of gonococcal growth in vitro (FIGS. 1 and 2), including complete growth inhibition of the multidrug-resistant isolate from Slovenia (FIG. 2). Surprisingly, NQNO did not compromise the growth of non-pathogenic *neisseria* species such as *Neisseria macacae* (FIG. 3) or the growth of commensal members of the human vaginal flora such as the gram-positive *Lactobacillus brevis* (FIG. 4).

Figure 11:
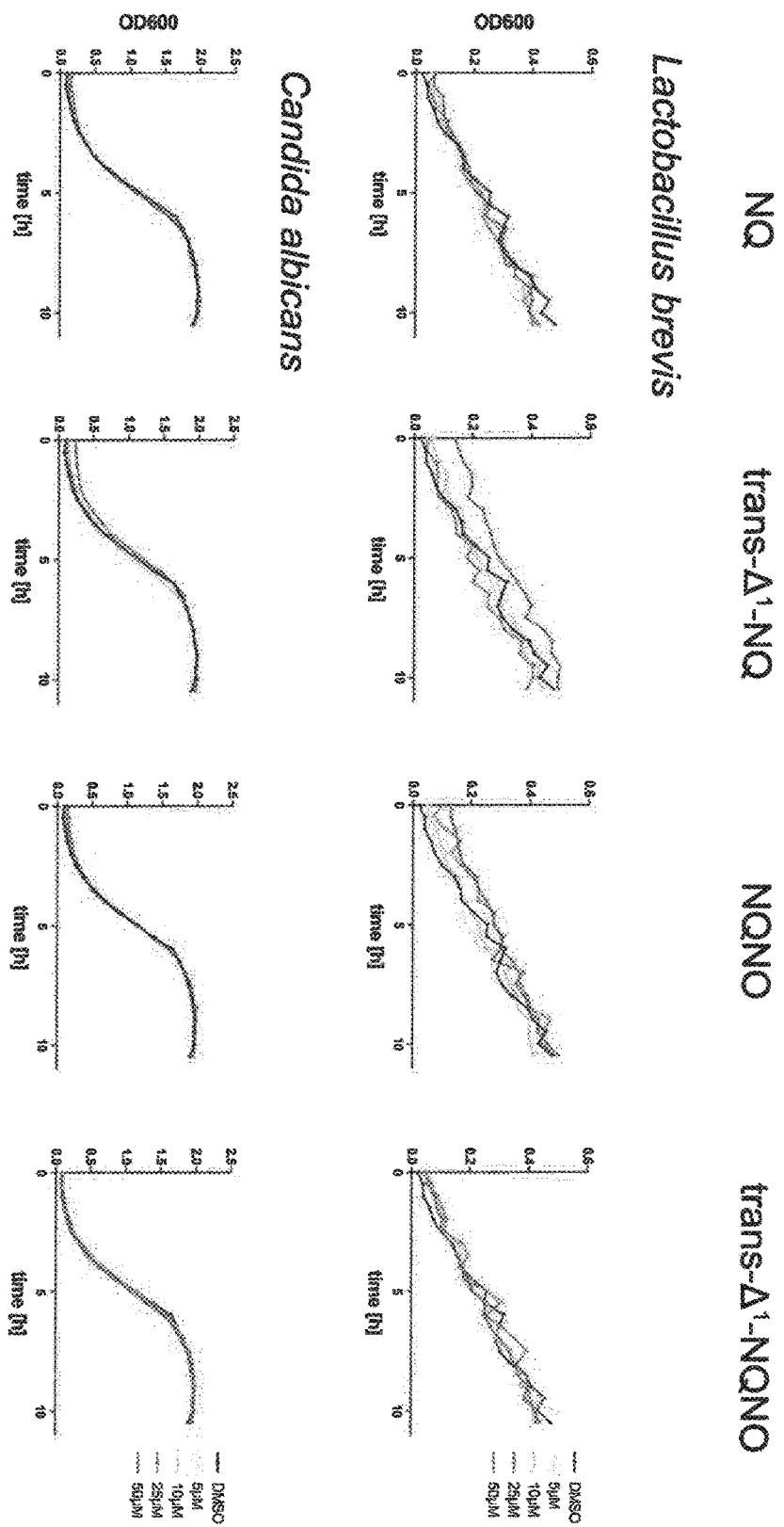
FIG. 11: Growth curves of *Lactobacillus brevis* and *Candida albicans* incubated with 5, 10, 25, and 50 μM of NO, trans-$\Delta^1$-NQ, NQNO, and trans-$\Delta^1$-NQNO (compounds represented by the Formulas (4), (6), (5), and (7)) for the indicated time in liquid culture. Optical density at 600 nm was determined every 30 minutes. Growth curves are displayed in comparison to cultures receiving solvent only (DMSO).

Example 2: Determination of the Inhibitory Effect of the Compounds Represented by the Formulas (4) to (7) Against Various Bacteria Growth experiments with the compounds represented by the Formulas (4) to (7) were conducted against various bacteria, including clinical isolates of *N. gonorrhoeae* including high priority $3^{rd}$ generation cephalosporin/fluoroquinolone-resistant strains, strains isolated from disseminated disease settings, and commensal *Neisseria* and other commensal bacteria and evaluated (FIGS. 5 and 11). Growth of the indicated bacteria was measured as described in Example 1. Growth inhibition was quantified by measuring the "area under the curve" in the presence of the indicated concentrations of the respective compound (5-50 μM) relative to growth in the presence of the solvent only. Black areas indicate growth inhibition with <30% growth compared to control. Commensal *Neisseria* are not compromised by NQNO, whereas all *N. gonorrhoeae* strains show either severe or complete growth inhibition in the presence of the compounds represented by the Formulas (4) to (7).

Figure 6:
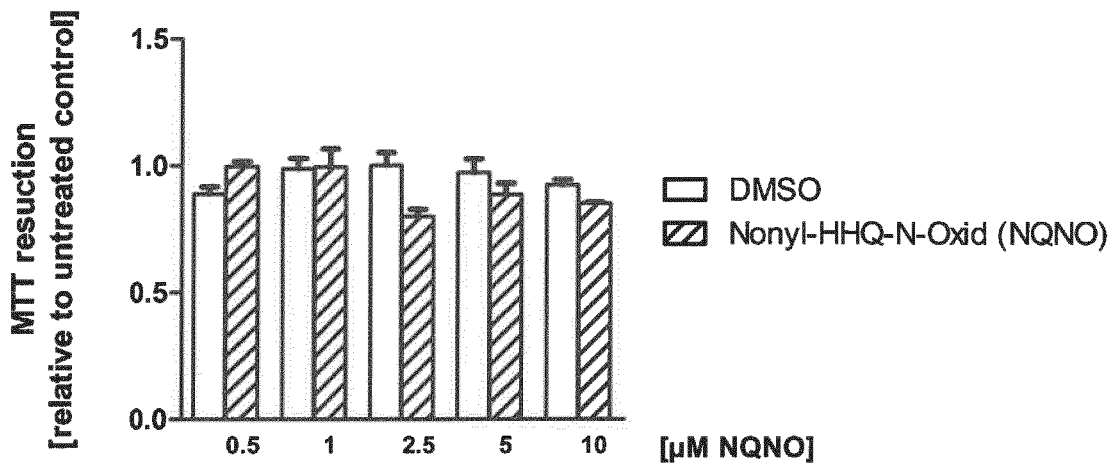
FIG. 6: Evaluation of potential cytotoxicity of NQNO towards human cells (HeLa cells).

Example 3: Cytotoxicity Test with NQNO (Compound Represented by the Formula (5)) and HeLa Cells as Well as Primary Human Vaginal Epithelial Cells Preliminary Experiments with HeLa Cells HeLa cells in 24-well plate were incubated for 24 h with concentrations of 0.5 to 10 μM NQNO or solvent (DMSO) as a control. Metabolic activity as a measure of mitochondrial respiration was recorded using 3-(4,5-Dimethylthiazol-2-yl)-2,5-diphenyltetrazoliumbromid (MTT) as reporting agent, Activity was measured with a plate reader at 550 nm, (FIG. 6). Shown are mean values+/S.D. of four replicate wells. Treatment with 10 μM NQNO up to 24 h does not lead to cytotoxicity in HeLa cells.

Cultivation of Eukaryotic Cells

HeLa S3 cells were cultivated in Dulbecco's modified Eagle's medium (DMEM) medium supplemented with 10% fetal calf serum and passaged every 2-3 days. Primary human vaginal epithelial cells (hVEC/MS74) were obtained from A. J. Schaeffer (Feinberg School of Medicine, Northwestern University, Chicago, Ill.) and are derived from vaginal tissue of a post-menopausal woman. The cell line was created through immortalization of these cells with human papilloma virus 16, E6 and E7 genes according to literature (N. Rajan et. al., Characterization of an immortalized human vaginal epithelial cell line. *J Urol* 163, 616-622 (2000)). MS74 were cultured on gelatine-coated cell culture dished using Dulbecco's modified Eagle's medium (DMEM) medium (biochrom) supplemented with 10% fetal calf serum, 1% non-essential amino acids and 1% pyruvate at 37° C. in 5% $CO_2$ and subcultured when half confluency was reached.

MTT Assay with Eukaryotic Cells

All plates were coated overnight at 4° C. with 0.1% gelatine in PBS before use. $2 \times 10^4$ HeLa S3 or MS74 cells were incubated with the mentioned concentrations of NQNO in 100 μl of their respective medium and incubated for 2 days at 37° C. and 5% $CO_2$. 10 μl of MTT solution (12 mM in PBS, sterile filtered with 0.2 μM filter) were added. The cells were subsequently incubated for 2 h at 37° C. Afterwards growth medium was removed and 100 μl isopropanol was added to each well. Formazan was allowed to dissolve overnight in a humidified chamber at room temperature. 0D550 was measured using a Thermo Fisher Varioskan Flash spectrophotometer.

Figure 12:
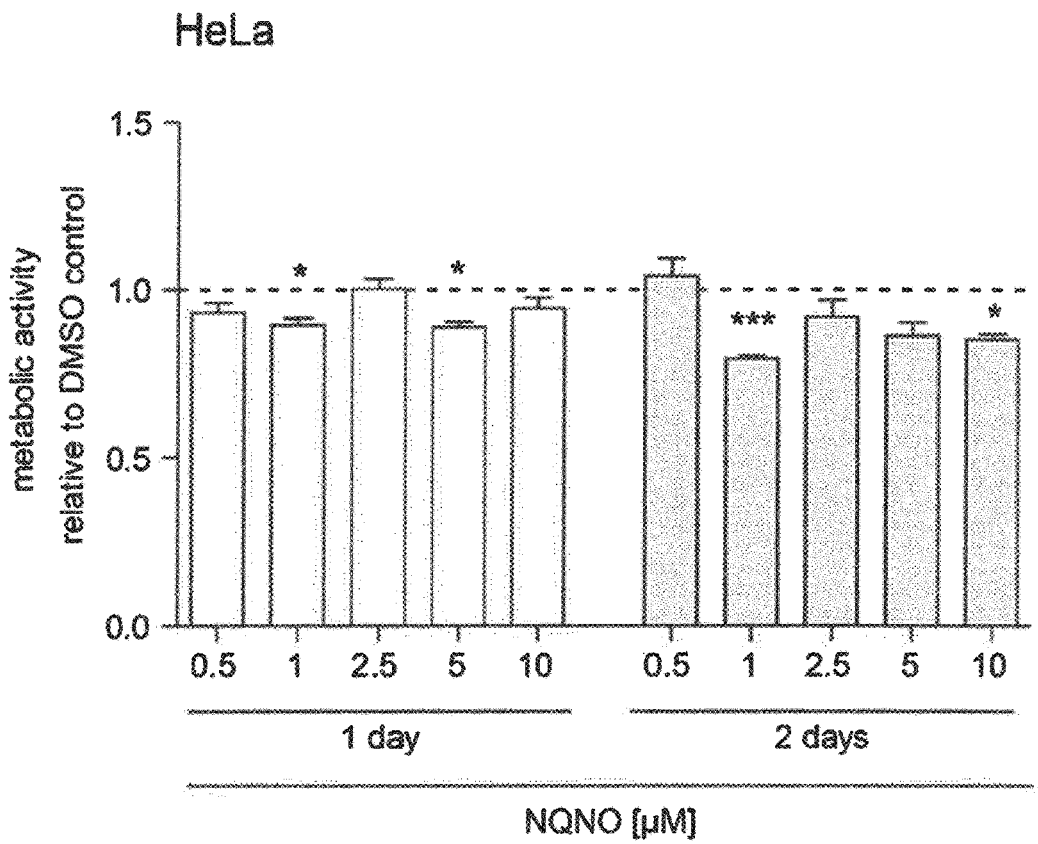
FIG. 12: Measurement of metabolic activity of HeLa cells upon treatment with 0.5, 1, 2.5, 5, and 10 μM NQNO for 1 or 2 days respectively. Samples were normalized to solvent (DMSO) treated cells, Assay was performed in technical triplicates: $*p<0.05$, $p<0.01$, $*p<0.001$.
Figure 13:
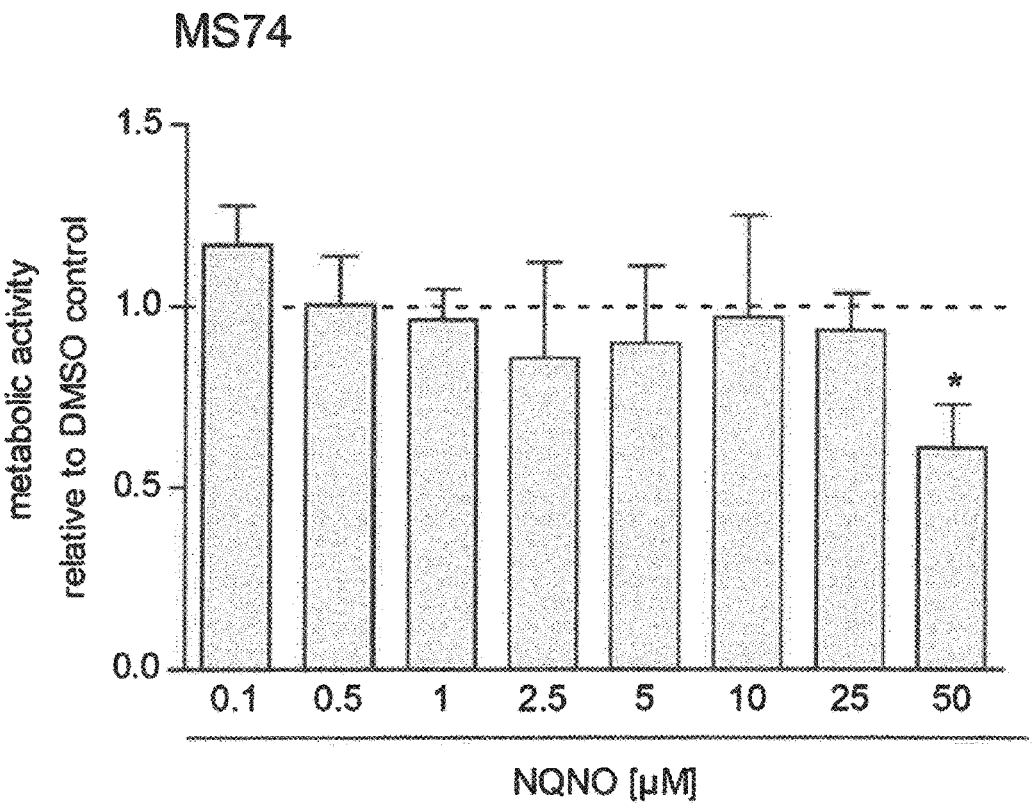
FIG. 13: Metabolic activity of MS74 cells upon treatment for 2 days with the indicated concentrations of NQNO was determined as in FIG. 12: Data show mean±SEM from three independent experiments; $*p<0.05$.
Figure 14:
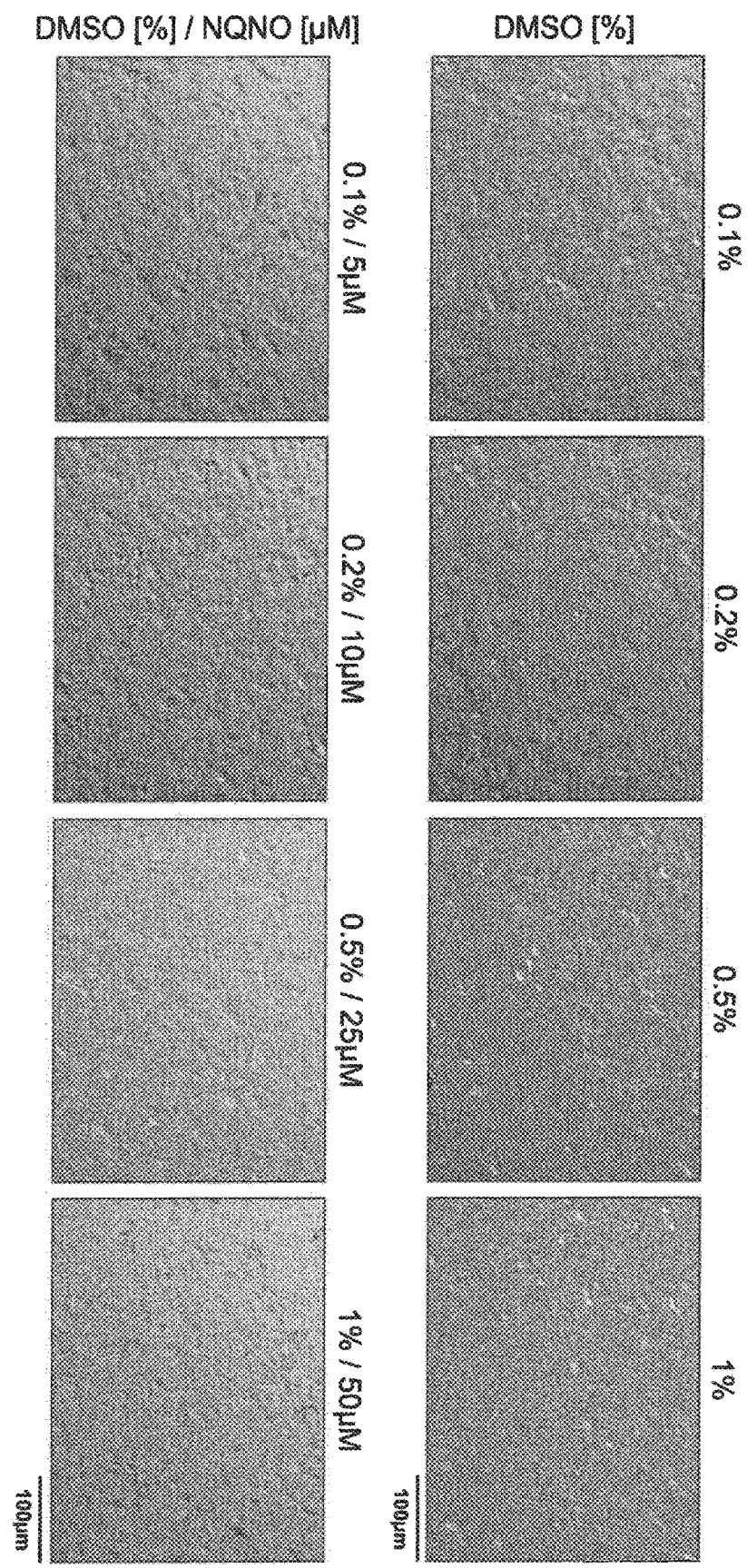
FIG. 14: Microscopic evaluation of MS74 cells treated for two days with the indicated concentrations of NQNO compared to DMSO control.

At concentrations up to 10 μM NQNO, cervical epithelial carcinoma cells (HeLa cells) did not exhibit signs of cytotoxicity over the course of 48 h (FIG. 12). Similarly, immortalized human vaginal epithelial cells (M574 cells) were also not harmed by concentrations of up to 25 μM NQNO and showed only slightly reduced metabolic activity when incubated for two days with 50 μM NQNO (FIG. 13). In a microscopic analysis, the morphology and overall phenotype of MS47 cells did not change upon treatment with up to 50 μM NQNO over the course of 2 days (FIG. 14).

Figure 7:
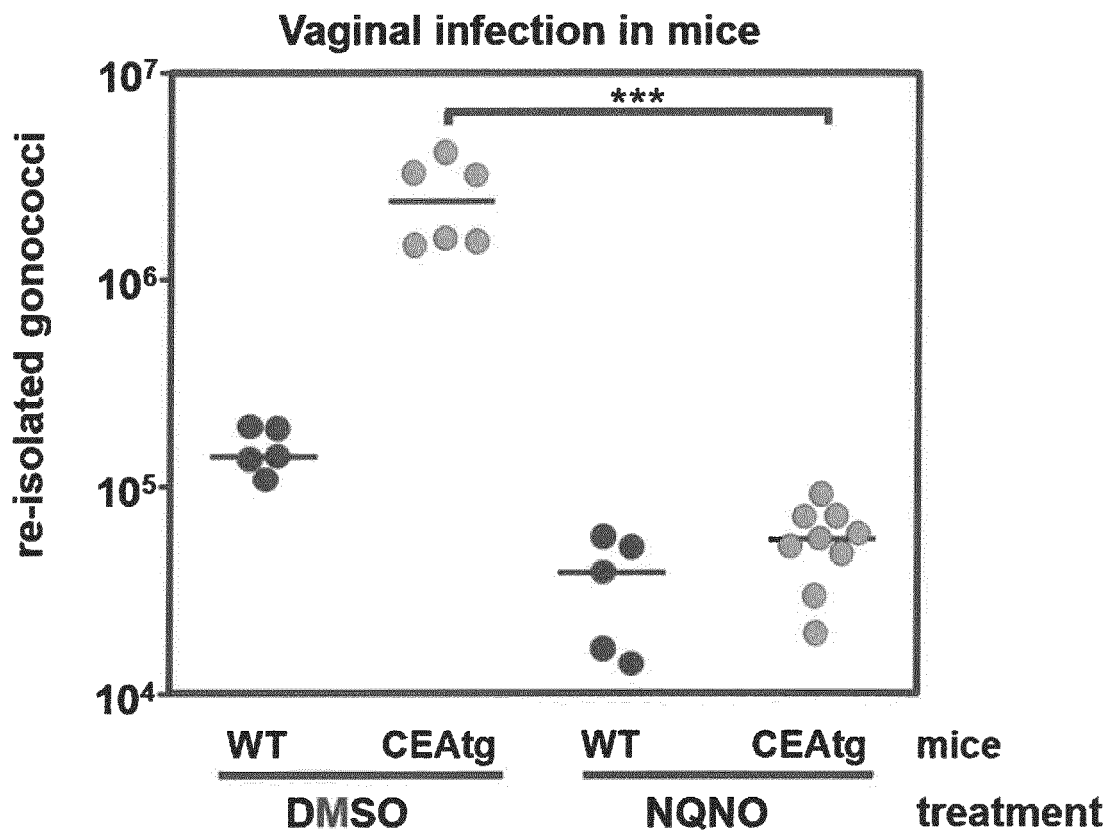
FIG. 7: Topical administration of NQNO completely blocks vaginal colonization by *Neisseria gonorrhoeae* in genetically modified mice (CEAtg) expressing human carcinoembryonic antigen (CEA), a receptor for the gonococcal Opa-adhesin, on their mucosal surface.

Example 4: Investigation Concerning the Effect of the Compound Used in the Present Invention in an Animal Model of Gonococcal Infection in Female Mice By using genetically modified mice (CEA-transgenic; CEAtg mice), which express a human receptor for the gonococcal Opa-adhesin on their mucosal surface, it is possible to study the initial colonization of the upper genital tract by *N. gonorrhoeae* and to re-isolate these pathogens after intra-vaginal challenge (FIG. 7). 6 to 8 week old, female wildtype (black) or CEA-transgenic (CEAtg, red) mice were infected with N. gonorrhoeae. 2 h after infection, the animals were treated with 20 µl buffer containing solvent (DMSO) or 50 µM NQNO (Compound represented by the Formula (5)). 20 h later, vaginal swaps were taken and plated on selective agar. Each dot refers to bacteria isolated from an individual animal (n≥5) (cf. FIG. 7). Re-isolated gonococcal colonies from control DMSO-treated animals confirm, that gonococci hardly colonize wildtype female mice, whereas approx. 30-fold higher numbers are found in CEAtg mice (cf. FIG. 7, left part). Treatment with NQNO significantly (***; p<0.001) reduces the number of re-isolated gonococci (FIG. 7). Thus, topical application of NQNO inhibited the ability of N. gonorrhoeae to colonize the genital tract.

In a further experiment, experimental vaginal infection of female mice with N. gonorrhoeae was performed as previously described in the literature (P. Muenzner, V. Bachmann, J. Hentschel, W. Zimmermann, C. R. Hauck, Human-restricted bacterial pathogens block shedding of epithelial cells by stimulating integrin activation. Science 329, 1197-1201 (2010)). Briefly, CEAtg mice were subcutaneously injected with 17-β-estradiol 4 days prior to infection. The drinking water was supplemented with trimethoprim sulphate (40 mg/100 ml) to reduce the overgrowth of commensal bacteria during hormone treatment. Mice were inoculated intravaginally with $10^8$ CFU (colony forming units) of OpaCEA expressing gonococci suspended in 20 µL of PBS. 1 h after infection, 10 µl of 25 µM or 50 µM NQNO (in PBS/1% DMSO) was applied intravaginally. Control mice received 10 µl PBS/1% DMSO only. 24 h later, the mucosa-associated bacteria were re-isolated by cotton swaps. Serial dilutions of re-isolated bacteria were plated on GC agar containing chloramphenicol (10 µg/ml) and erythromycin (7 µg/ml) and the colonies were counted after 20 h of incubation at 37° C., 5% $CO_2$.

Figure 15:
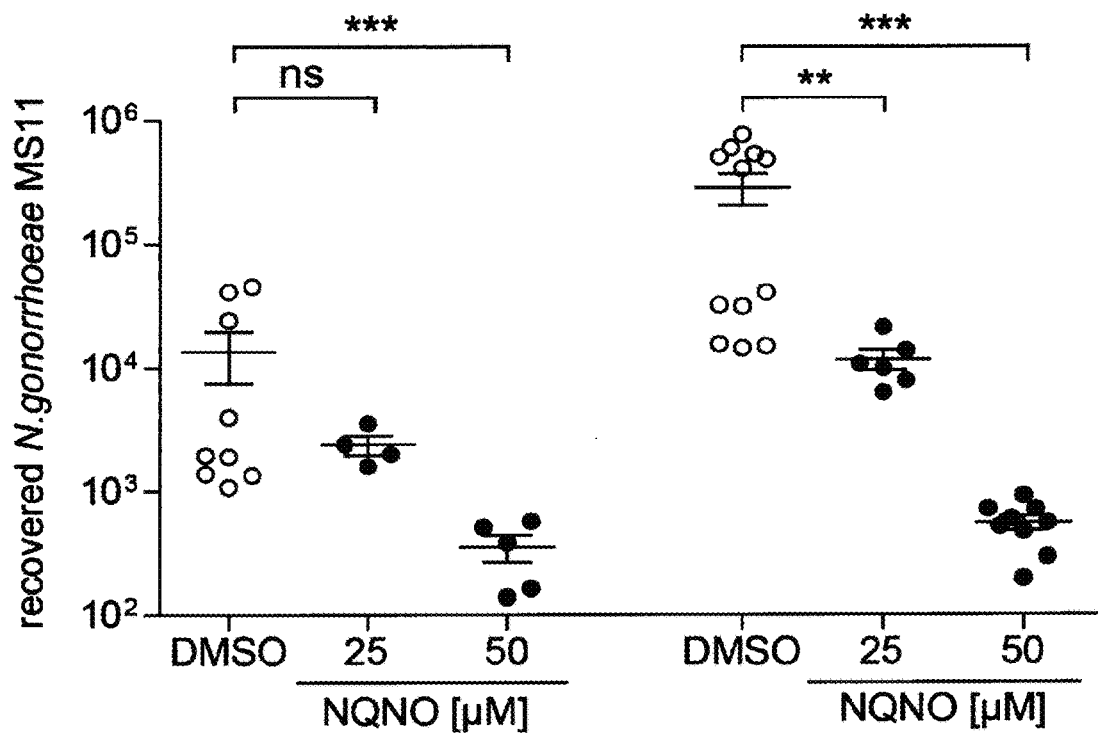
FIG. 15: Wildtype or CEAtg female mice were infected with OpaCEA-expressing gonococci for 1 h, before they were treated with 10 μl of 25 μM or 50 μM NQNO. Controls received solvent (DMSO). After 24 hours, bacteria colonizing the genital tract were collected by a cotton swab and plated on agar. Data show bacterial colonies isolated from individual mice from two independent experiments. Mean values ±SEM are indicated by horizontal bars. Differences between groups were determined by Mann Whitney test: $p<0.01$, $*p<0.001$.

Only low numbers of gonococci could be re-isolated from wildtype animals, whereas 50-100 fold more bacteria were recovered from the genital tract of CEAtg mice receiving solvent (FIG. 15). Importantly, when CEAtg mice were treated with NQNO, hardly any gonococci could be re-isolated (FIG. 15).

Figure 8:
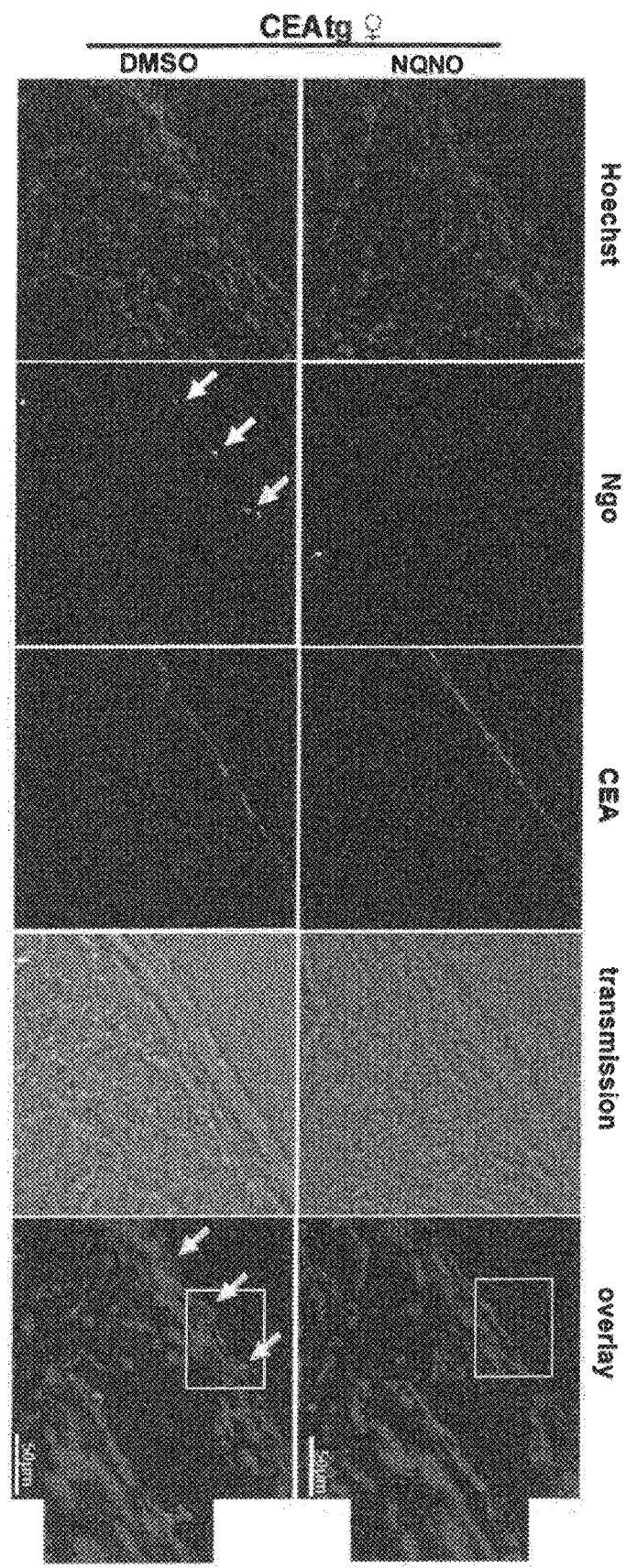
FIG. 8: Immunofluorescence staining of tissue sections obtained from the upper vaginal tract of infected CEAtg animals being treated with NQNO (50 μM dissolved in DMSO) or with solvent (DMSO) only. The genital tract was excised and cryosections were stained for cell nuclei (Hoechst), human CEA, and *N. gonorrhoeae* (Ngo, arrows).

Example 5: Immunofluorescence Staining of Tissue Sections Obtained from the Upper Vaginal Tract of Infected Treated/Untreated CEAtg Animals 6 to 8 week old, female CEA-transgenic mice were infected with N. gonorrhoeae. 2 h after infection, the animals were treated with 20 µl buffer containing solvent (DMSO) or 50 µM NQNO (Compound represented by the Formula (5)). 20 h later, the genital tract was excised and cryosections were stained for cell nuclei (Hoechst; blue), human CEA (red) and N. gonorrhoeae (gonococci, green) (FIG. 8). Fluorescence microscopy (Muenzner P, Bachmann V, Zimmermann W, Hentschel J, Hauck CR. (2010) Human-restricted bacterial pathogens block shedding of epithelial cells by stimulating integrin activation. Science. 329(5996): 1197-201) revealed numerous gonococci on the mucosal surface of DMSO-treated animals (FIG. 8; arrows), while hardly any gonococci could be detected in NQNO-treated animals. In both samples, staining of human CEA, which is expressed by the upper epithelial cell layers in the urogenital tract of the transgenic animals, shows a continuous and unaltered mucosal surface (FIG. 8) and, thus, demonstrates the integrity of the epithelial cell layer after infection and NQNO-treatment.

Figure 9:
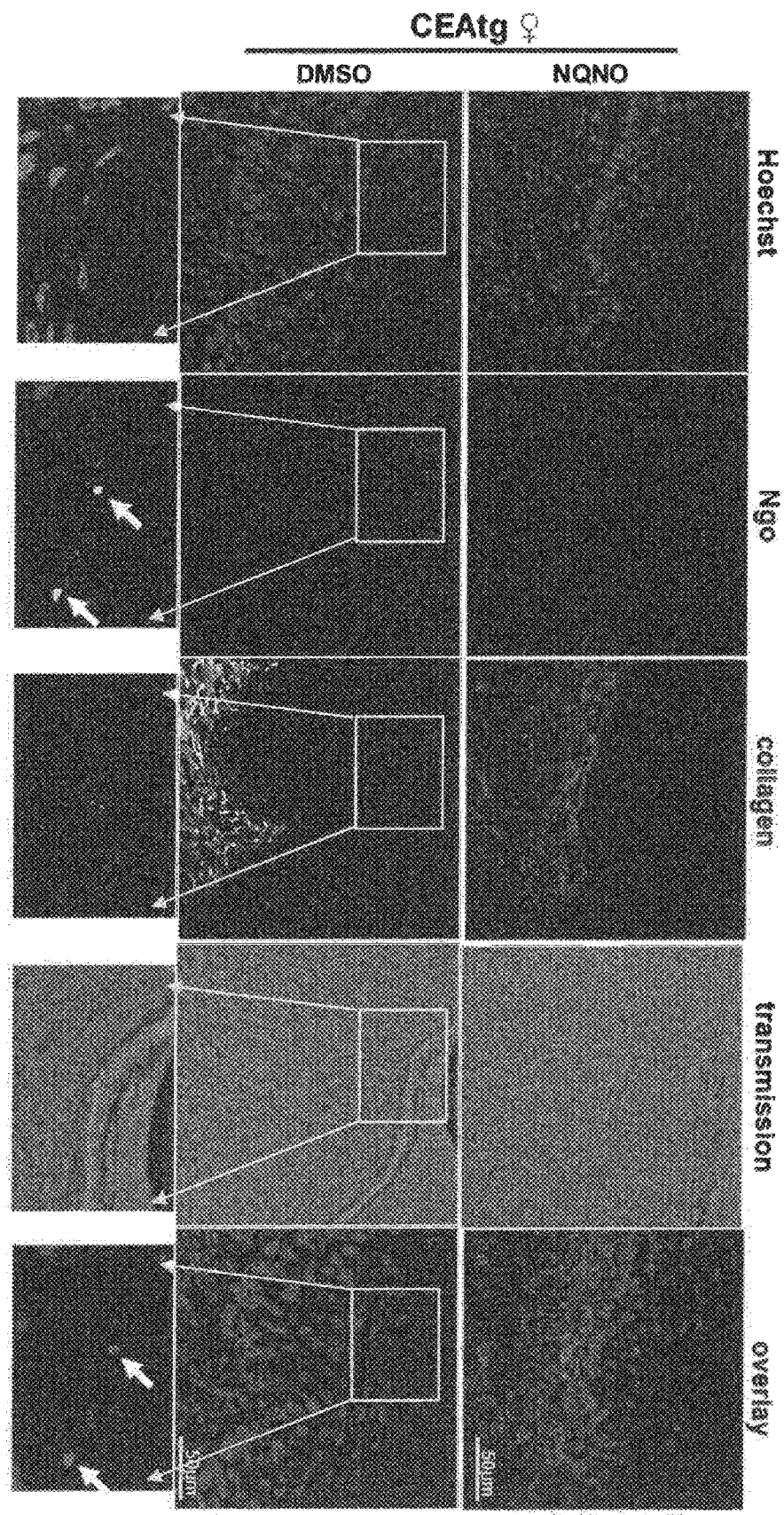
FIG. 9: Immunofluorescence staining of tissue sections obtained from the upper vaginal tract of infected CEAtg animals being treated with NQNO (50 μM dissolved in DMSO) or with solvent (DMSO) only. The genital tract was excised and cryosections were stained for cell nuclei (Hoechst), collagen in the connective tissue, and *N. gonorrhoeae* (Ngo, arrows).

Additional cryosections from the same samples were stained for cell nuclei (Hoechst; blue), human collagen (red) and N. gonorrhoeae (gonococci, green) (FIG. 9). Fluorescence microscopy again demonstrated numerous gonococci on the mucosal surface of DMSO-treated animals (FIG. 9; arrows); while no gonococci could be detected in NQNO-treated animals. Moreover, collagen staining reveals the intact subepitheial tissue without signs of tissue destruction by the application of NQNO indicating that topical administration of NQNO does not damage the mucosal surface.

In particular, in the above experiments the genital tract of infected mice was excised and immediately fixed with 4% paraformaldehyde for at least 24 h. The fixed tissue was sequentially transferred to 10% sucrose, 0.05% cacodylic acid for 1 h at 4° C., to 20% sucrose for 1 h at 4° C., and then into 30% sucrose at 4° C. overnight. Organs were mounted in the embedding medium (Cryo-M-Bed; Bright Instrument, Huntingdon, UK) and frozen at −20° C. 10 µm thick sections were cut at −20° C. using a cryostat (Vacutom HM500, Microm, Germany). Sections were stained with a mouse monoclonal antibody against collagen type IV (clone M3F7; dilution 1:200) together with a polyclonal rabbit antibody against N. gonorrhoeae (dilution 1:100). Detection of the primary antibodies was done with a combination of Cy5-conjugated goat-anti-rabbit antibody (1:250) and Cy3-conjugated goat-anti mouse antibody (1:250). Cell nuclei were visualized by the addition of Hoechst 33342 (1:30,000; Life Technologies, Darmstadt, Germany) in the final staining step.

Example 6: Histological Examination of Tissue Sections Obtained from the Upper Vaginal Tract of Treated/Untreated CEAtg Animals 6 to 8 week old, female CEA-transgenic mice were treated with 20 µl buffer containing solvent (DMSO) or 50 µM NQNO (Compound represented by the Formula (5)). 20 h later, the genital tract was excised, fixed, paraffin embedded and tissue sections were stained with HE (Haematoxilin/Eosin) solution. Microscopic examination reveals an intact striated epithelium of the vaginal tract in both the DMSO as well as the NQNO-treated animals.

In particular, in the above experiment the genital tract of infected and NQNO/DMSO or DMSO treated animals was excised and placed in 4% neutral buffer containing formalin overnight followed by 0.4% PFA (paraformaldehyde) treatment. The tissue was then dehydrated and embedded in paraffin. 10 µm serial sections were cut, deparaffinized and rehydrated in a graded series (100% to 75%) of ethanol. Sections were serially stained with Hematoxilin solution according to Mayer (Sigma) and 0.5% Eosin G solution (Roth).

Figure 10:
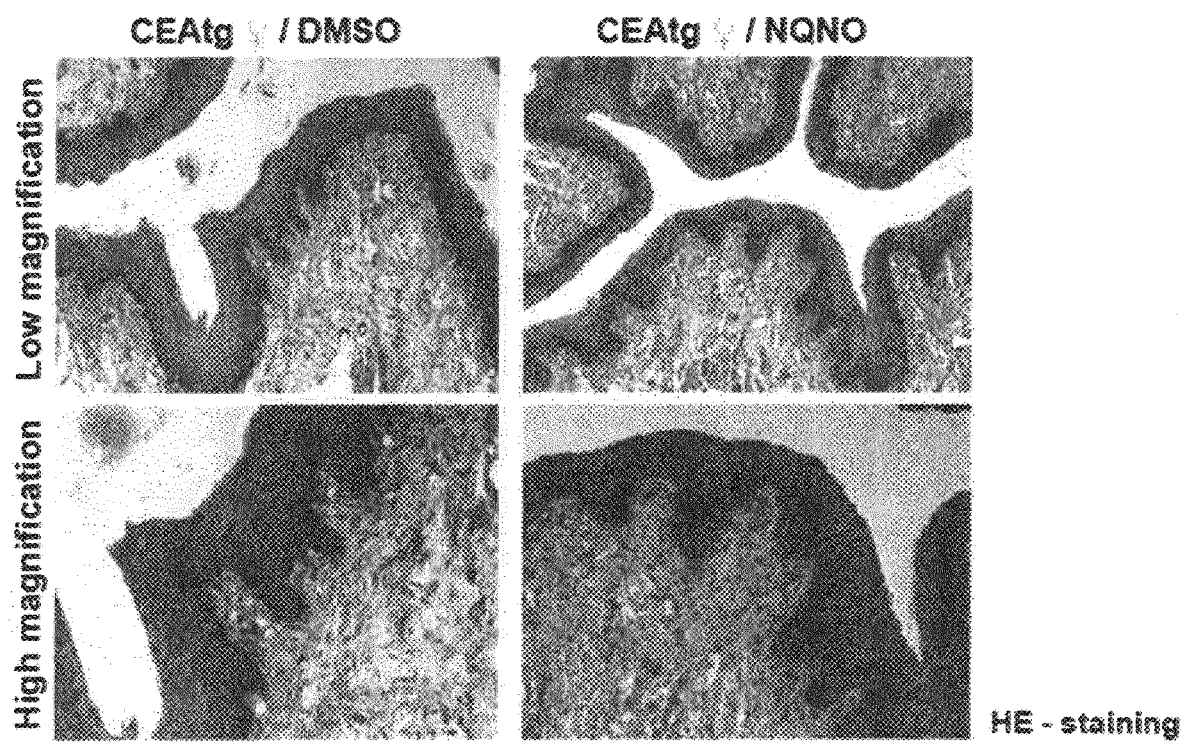
FIG. 10: Haematoxilin/Eosin (HE) staining of tissue sections obtained from the upper vaginal tract of CEAtg animals being treated with NQNO (50 μM dissolved in DMSO) or with solvent (DMSO) only. The genital tract was excised, fixed, paraffin embedded and sections were stained to reveal the overall integrity of the epithelial and subepithelial tissue.

Together, the findings presented in Examples 4-6 not only corroborate the strong reduction in bacterial burden upon NQNO treatment in vivo, but also demonstrate that the epithelial surface is not damaged or compromised by the topical application of NQNO at bactericidal concentrations. The macroscopic observation of treated animals as well as the histological analysis of paraffin sections of the infected tissue also indicate that topical application of the compounds is well tolerated and does not result in damage of the female vaginal epithelium (FIG. 10). Furthermore, all mice receiving NQNO did not show any signs of discomfort, demonstrating that a single topical application of this compound is well tolerated and is sufficient to eliminate gonococci from the vaginal tract. These results demonstrate that the compound of the present invention can be used for treating infections with pathogenic *Neisseria* species, preferably *N. gonorrhoeae*, e.g. by use as gonococcicidal therapeutics.

Example 7: Stability of NQNO in Solvent

Figure 16:
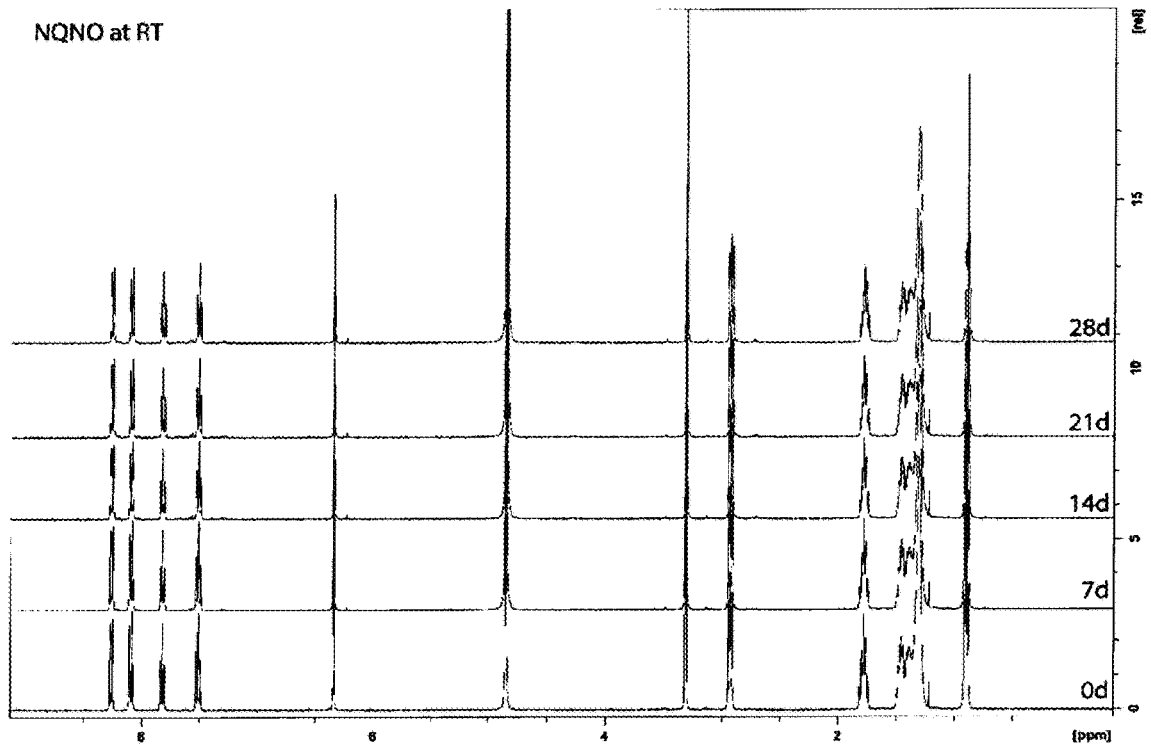
FIG. 16: Proton NMR spectra showing the stability of NQNO in deuterated methanol at a final concentration of 25 mM. Samples were incubated for 28 days at 25° C. A spectrum was measured every seventh day and compared with the previous measurements.
Figure 17:
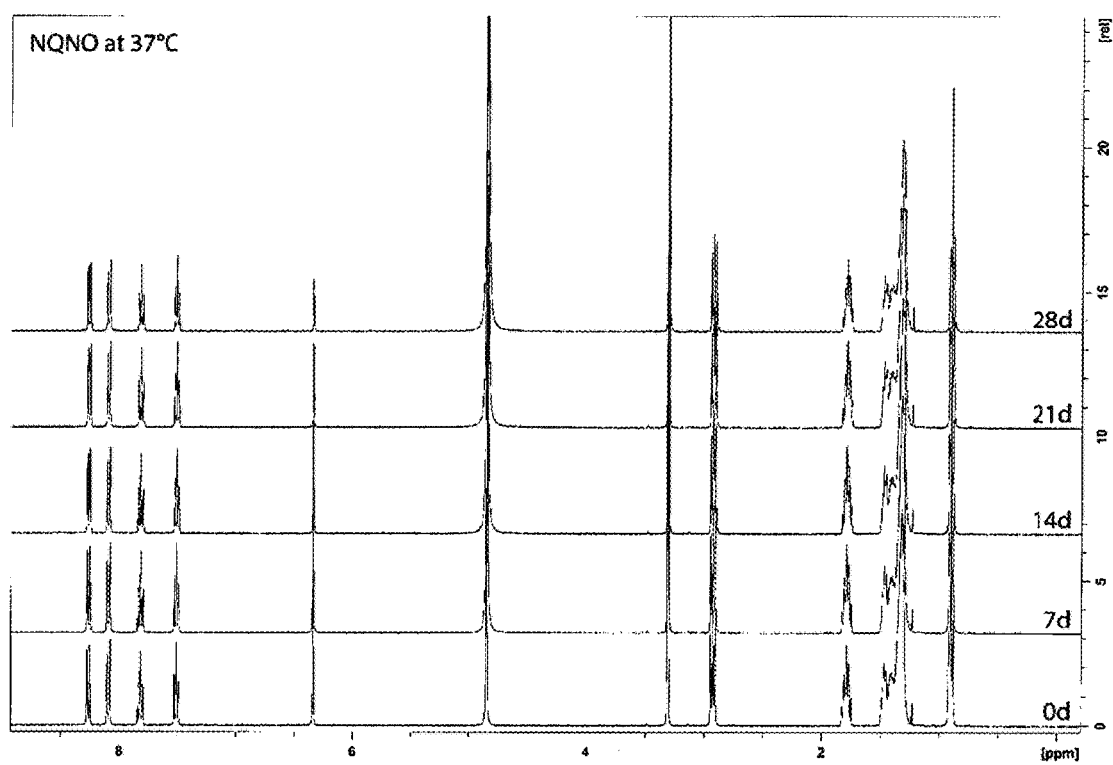
FIG. 17: Proton NMR spectra showing the stability of NQNO in deuterated methanol at a final concentration of 25 mM. Samples were incubated for 28 days at 37° C. A spectrum was measured every seventh day and compared with the previous measurements.

Two samples of NQNO were dissolved in deuterated methanol (CD$_3$OD) to reach a final concentration of 25 mM. Samples were kept at 25° C. or 37° C. for 28 days and proton NMR spectra were measured with the same acquisition parameters every week and the spectra compared with the ones from day 0. The results are given in FIGS. 16 and 17 and show that NQNO is stable at 37° C. in deuterated methanol for at least one month.

Example 8: Stability of NQNO in Cell Culture Medium

Figure 18:
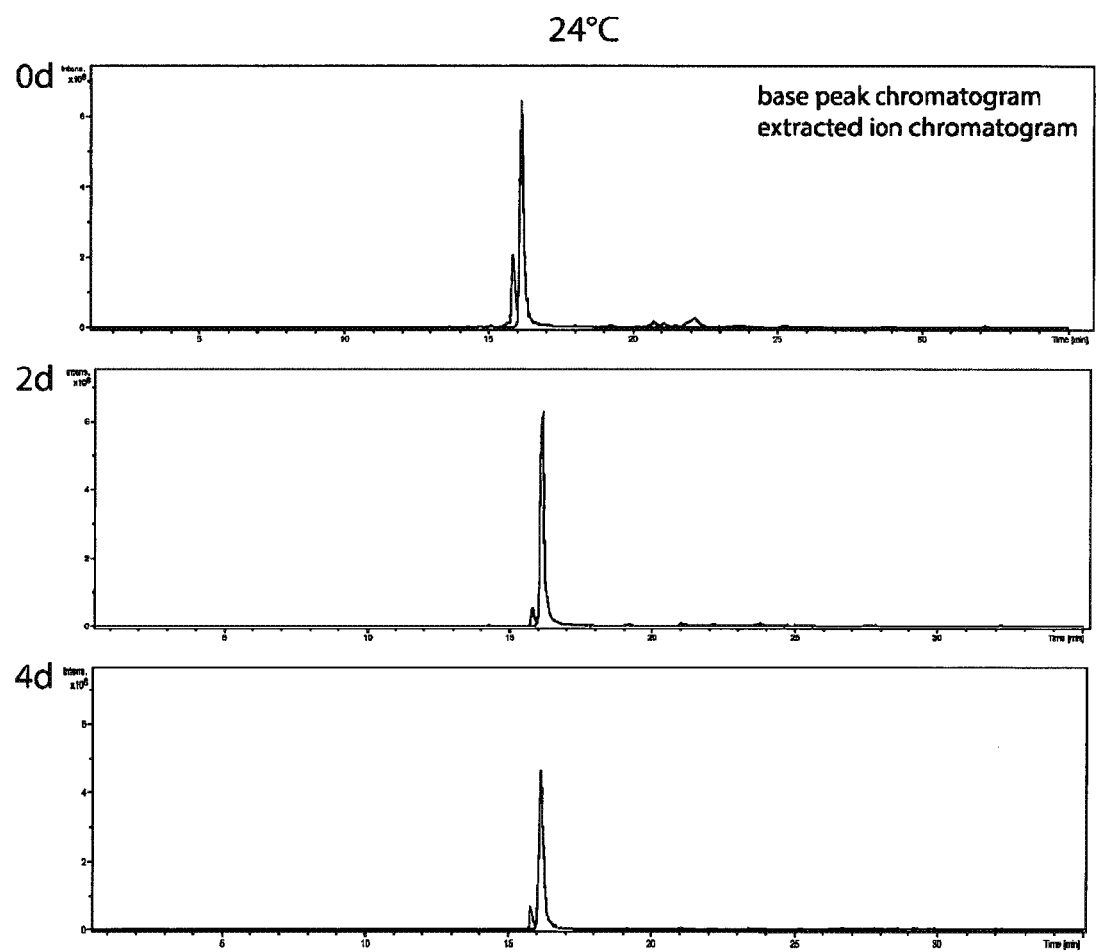
FIG. 18: Stability of 100 μM NQNO in Dulbecco's modified Eagle's medium (DMEM) medium supplemented with 10% fetal calf serum. Samples were incubated at 24° C. for 4 days. Samples were taken at day 0 and every second day. Samples were analysed by LC-MS and the integrals of the detected NQNO (by using extracted ion chromatograms) compared to the integral of the control (100 μM NQNO in $H_2O$) which was set to 100%.
Figure 19:
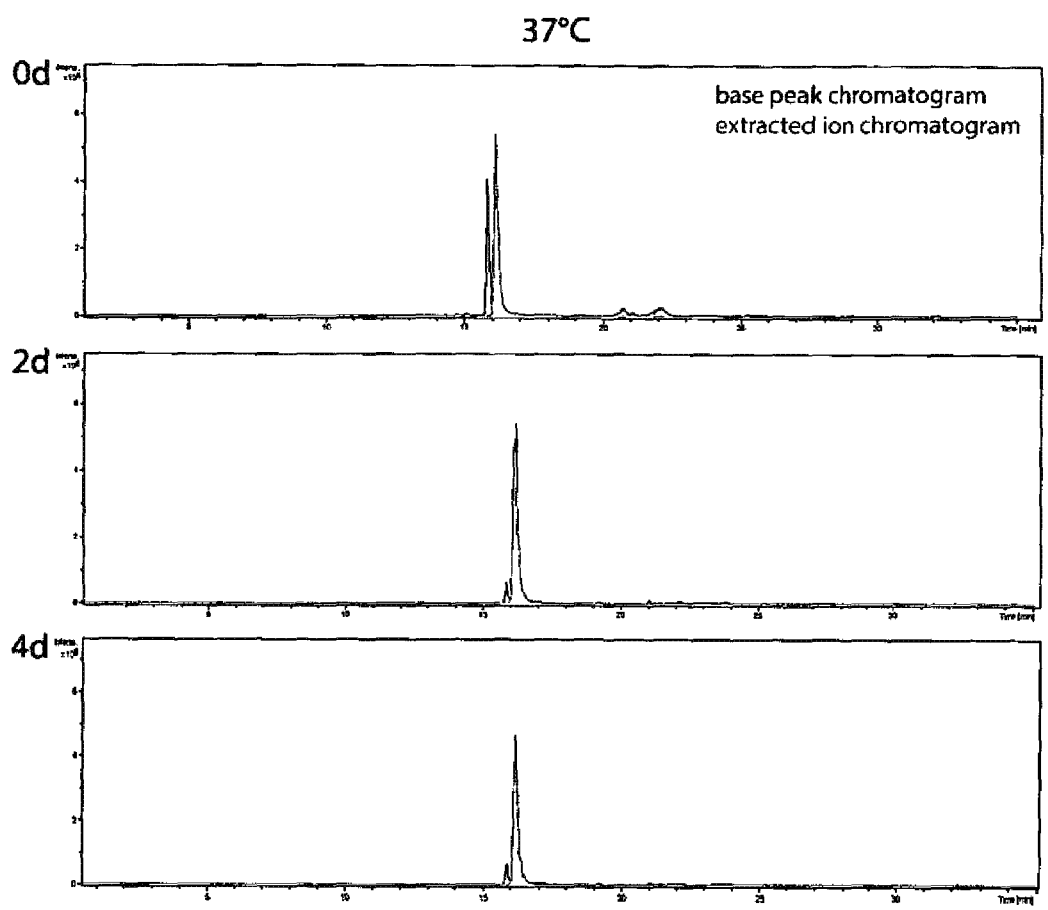
FIG. 19: Stability of 100 μM NQNO in Dulbecco's modified Eagle's medium (DMEM) medium supplemented with 10% fetal calf serum. Samples were incubated at 37° C. for 4 days. Samples were taken at day 0 and every second day. Samples were analysed by LC-MS and the integrals of the detected NQNO (by using extracted ion chromatograms) compared to the integral of the control (100 μM NQNO in $H_2O$) which was set to 100%.
Figure 20:
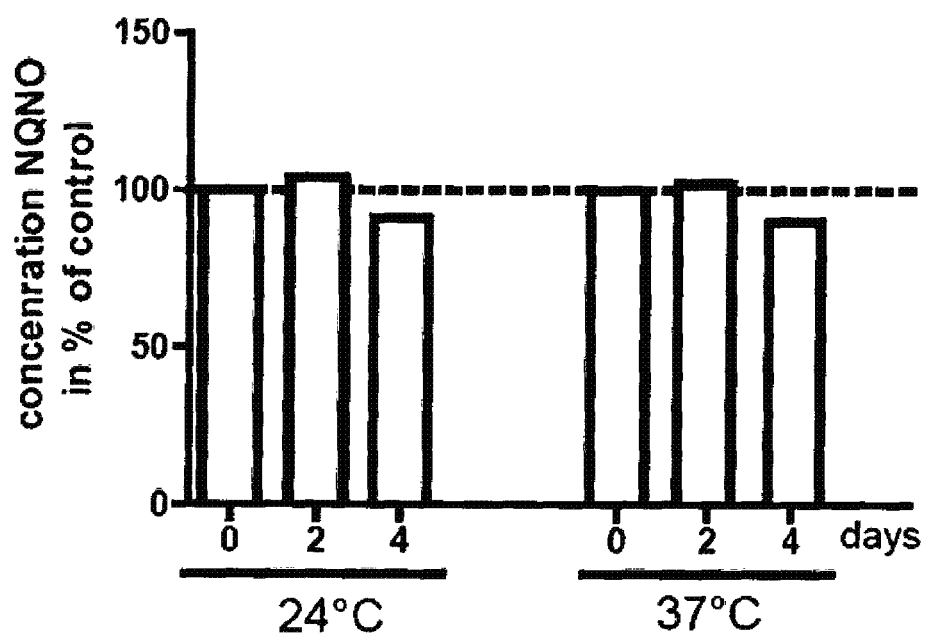
FIG. 20: Quantification of the results of FIGS. 18 and 19, normalized to control levels.

Stability of 100 μM NQNO in Dulbecco's modified Eagle's medium (DMEM) medium supplemented with 10% fetal calf serum at 24° C. and 37° C. was evaluated over a period of 4 days. Samples were taken at the beginning (day 0) and every second day. Samples were analyzed by LC-MS and the integrals of the detected NQNO (by using extracted ion chromatograms) compared to the integral of the control (100 μM NQNO in H$_2$O) which was set to 100%. The results are given in FIGS. 18 to 20 and show that NQNO is stable in serum-containing cell culture medium for at least 4 days.

-continued
Formula (7)
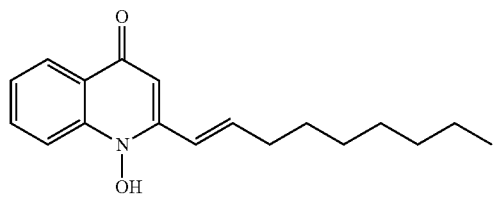

The invention claimed is:

1. A method for preventing or treating infections from a pathogen selected from *Neisseria* species, *Haemophilus* species and *Moraxella catarrhalis* in a mammal, the method comprising administering to said mammal a composition comprising a compound represented by the general Formula (1) or a pharmaceutically acceptable salt thereof

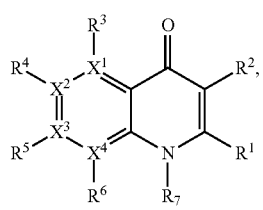

(Formula (1))

wherein
  $R^1$ is selected from the group consisting of a substituted or unsubstituted alkyl group having from 3 to 20 carbon atoms, a substituted or unsubstituted cycloalkyl group having from 4 to 12 carbon atoms, a substituted or unsubstituted alkenyl group having from 3 to 20 carbon atoms, a substituted or unsubstituted cycloalkenyl group having from 4 to 12 carbon atoms, a substituted or unsubstituted alkynyl group having from 3 to 20 carbon atoms, a substituted or unsubstituted aryl group, and a substituted or unsubstituted heteroaryl group;
  $R^7$ is selected from the group consisting of a hydrogen atom, a methyl group, and —OH;
  $R^2$ is selected from the group consisting of a hydrogen atom, a substituted or unsubstituted alkyl group having 1 to 4 carbon atoms, a halogen atom, —NZ$^1$Z$^2$, —NO$_2$, and —OZ$^3$, wherein $Z^1$ to $Z^3$ are each independently selected from the group consisting of a hydrogen atom and a methyl group;
  $X^1$ to $X^4$ are each independently selected from a carbon atom and a nitrogen atom with the proviso that the respective $R^3$ to $R^6$ is absent, when the corresponding $X^1$ to $X^4$ is a nitrogen atom, and wherein at most two of $X^1$ and $X^4$ is/are a nitrogen atom; and
  $R^3$ to $R^6$, when present, are each independently selected from the group consisting of a hydrogen atom, a methyl group, a fluorine atom, and —OE$^3$, wherein $E^3$ is selected from the group consisting of a hydrogen atom, and a methyl group.

2. The method according to claim 1, wherein $R^1$ is selected from the group consisting of a substituted or unsubstituted alkyl group having from 3 to 20 carbon atoms, a substituted or unsubstituted alkenyl group having from 3 to 20 carbon atoms, and a substituted or unsubstituted alkynyl group having from 3 to 20 carbon atoms.

3. The method according to claim 2, wherein $R^1$ is a nonyl group or a nonenyl group.

4. The method according to claim 1, wherein $R^2$ is selected from the group consisting of a hydrogen atom, a substituted or unsubstituted alkyl group having 1 to 4 carbon atoms, a halogen atom, —CF$_3$, —NH$_2$, and —OH.

5. The method according to claim 4, wherein $R^2$ is a hydrogen atom.

6. The method according to claim 1, wherein $X^1$ to $X^4$ are each a carbon atom.

7. The method according to claim 1, wherein $R^3$ to $R^6$, when present, are each a hydrogen atom.

8. The method according to claim 1, wherein $R^7$ is a hydrogen atom or OH.

9. The method according to claim 1, wherein the compound is selected from the group consisting of the compounds represented by the following Formulas (2) to (7), or a pharmaceutically acceptable salt thereof:

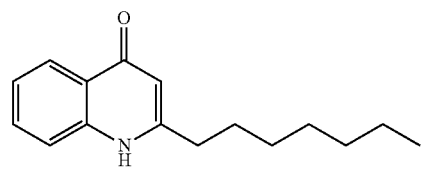

Formula (2)

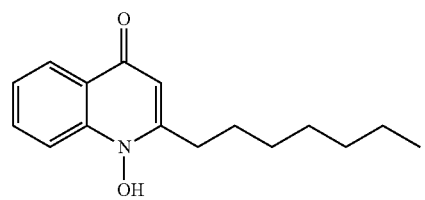

Formula (3)

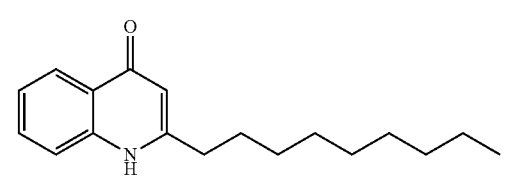

Formula (4)

-continued

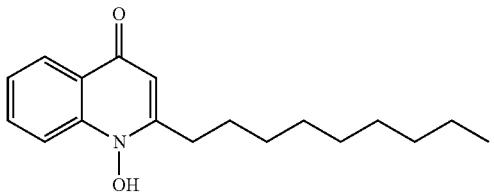
Formula (5)

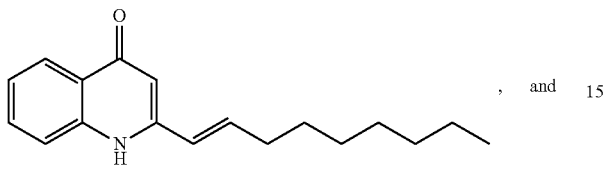
, and
Formula (6)

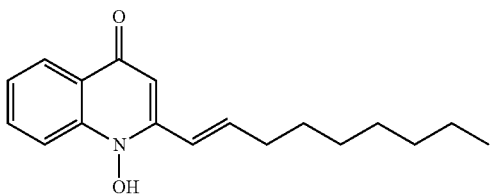
.
Formula (7)

10. The method according to claim 1, wherein the *Neisseria* species are selected from the group consisting of *Neisseria gonorrhoeae*, *Neisseria meningitidis*, and *Neisseria lactamica*.

11. The method according to claim 10, wherein the *Neisseria* species are pathogenic multidrug-resistant *Neisseria* species.

12. The method according to claim 1, wherein the mammal is a human.

13. A method for disinfecting a substrate from a pathogen selected from *Neisseria* species, *Haemophilus* species and *Moraxella catarrhalis*, the method comprising disinfecting the substrate with a compound represented by the general Formula (1) or a pharmaceutically acceptable salt thereof

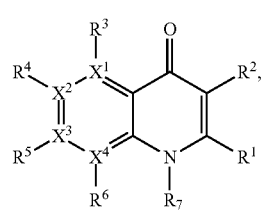
(Formula (1))

wherein
$R^1$ is selected from the group consisting of a substituted or unsubstituted alkyl group
having from 3 to 20 carbon atoms, a substituted or unsubstituted cycloalkyl group
having from 4 to 12 carbon atoms, a substituted or unsubstituted alkenyl group
having from 3 to 20 carbon atoms, a substituted or unsubstituted cycloalkenyl group
having from 4 to 12 carbon atoms, a substituted or unsubstituted alkynyl group
having from 3 to 20 carbon atoms, a substituted or unsubstituted aryl group, and a substituted or unsubstituted heteroaryl group;

$R^7$ is selected from the group consisting of a hydrogen atom, a methyl group, and —OH;

$R^2$ is selected from the group consisting of a hydrogen atom, a substituted or unsubstituted alkyl group having 1 to 4 carbon atoms, a halogen atom, —$NZ^1Z^2$, —$NO_2$, and —$OZ^3$, wherein $Z^1$ to $Z^3$ are each independently selected from the group consisting of a hydrogen atom and a methyl group;

$X^1$ to $X^4$ are each independently selected from a carbon atom and a nitrogen atom with the proviso that the respective $R^3$ to $R^6$ is absent, when the corresponding $X^1$ to $X^4$ is a nitrogen atom, and wherein at most two of the $X^1$ and $X^4$ is/are a nitrogen atom; and $R^3$ to $R^6$, when present, are each independently selected from the group consisting of a hydrogen atom, a fluorine atom and —$OE^3$, wherein $E^3$ is selected from the group consisting of a hydrogen atom and a methyl group; and the substrate is selected from the group consisting of medical tools, medical equipment, floor, linen, paper, and medical and industrial surfaces.

14. The method according to claim 13, wherein the compound is selected from the group consisting of the compounds represented by the following Formulas (2) to (7), or a pharmaceutically acceptable salt thereof:

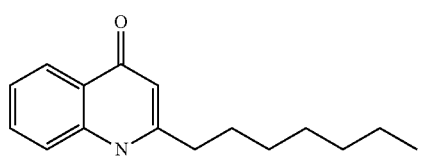
Formula (2)

,

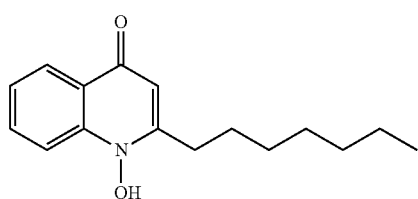
Formula (3)

,

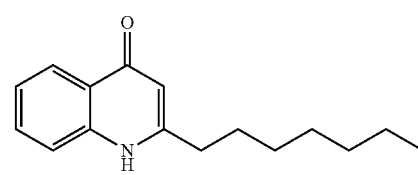
Formula (4)

,

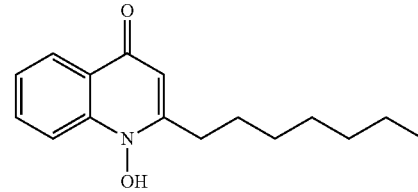
Formula (5)

,

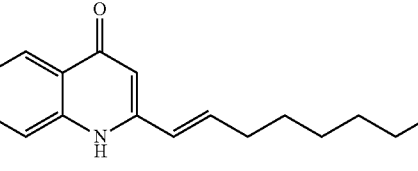
Formula (6)

, and

Formula (7)

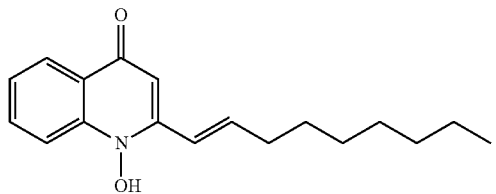

15. The method according to claim 1, wherein the compound is present in a pharmaceutically active amount, and wherein the composition optionally includes a pharmaceutically acceptable carrier, excipient or diluent.

16. A method for treating infections from a pathogen selected from *Neisseria* species, *Haemophilus* species and *Moraxella catarrhalis* in a mammal, the method comprising administering to said mammal a composition comprising a compound selected from the group consisting of the compounds represented by the following Formulas (2) to (7), or a pharmaceutically acceptable salt thereof:

Formula (2)

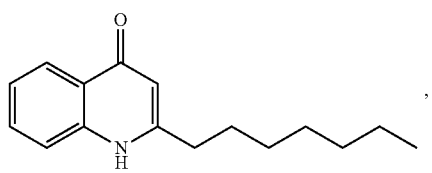

Formula (3)

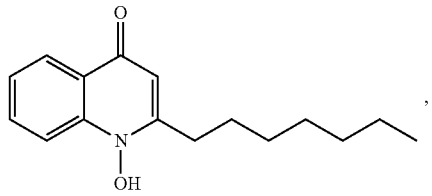

Formula (4)

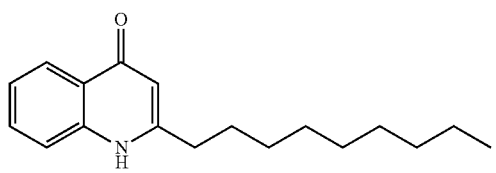

Formula (5)

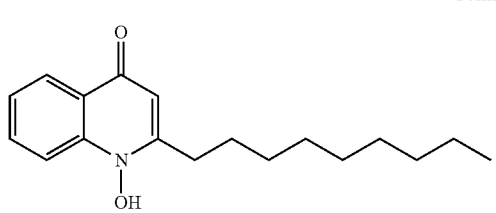

Formula (6)

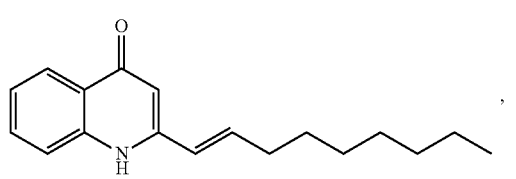, and

Formula (7)

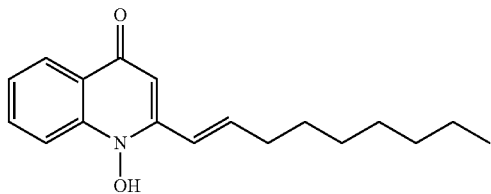

17. A method for disinfecting a substrate from a pathogen selected from *Neisseria* species, *Haemophilus* species and *Moraxella catarrhalis*, the method comprising disinfecting the substrate with a compound selected from the group consisting of the compounds represented by the following Formulas (2) to (7), or a pharmaceutically acceptable salt thereof:

Formula (2)

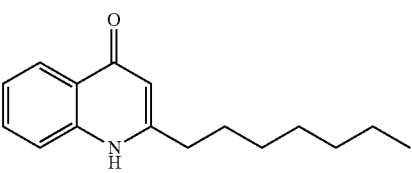

Formula (3)

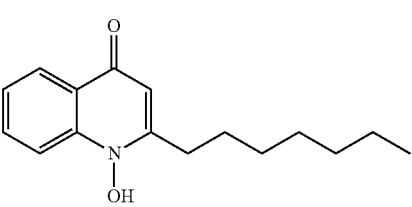

Formula (4)

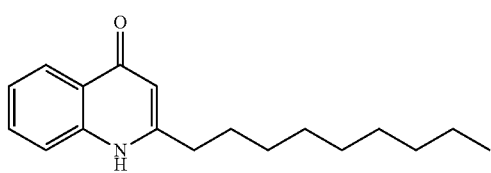

Formula (5)

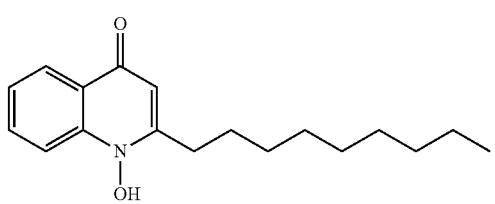

Formula (6)

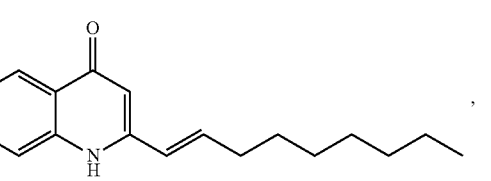, and